(12) United States Patent
Lindsay et al.

(10) Patent No.: US 6,700,034 B1
(45) Date of Patent: Mar. 2, 2004

(54) ABSORBENT ARTICLE WITH UNITARY ABSORBENT LAYER FOR CENTER FILL PERFORMANCE

(75) Inventors: Jeffrey Dean Lindsay, Appleton, WI (US); Fung-jou Chen, Appleton, WI (US); Joseph DiPalma, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/411,261

(22) Filed: Oct. 1, 1999

(51) Int. Cl.⁷ ............................. A61F 13/15; A61F 13/20
(52) U.S. Cl. ........................... 604/378; 604/367
(58) Field of Search ................... 604/367, 370, 604/378, 385.01, 385.101

(56) References Cited

U.S. PATENT DOCUMENTS

| | | |
|---|---|---|
| 2,064,431 A | 12/1936 | Jurgensen |
| 2,683,457 A | 7/1954 | Cunningham |
| 2,747,575 A | 5/1956 | Mercer |
| 3,126,888 A | 3/1964 | Woldman |
| 3,156,242 A | 11/1964 | Crowe, Jr. |
| 3,294,091 A | 12/1966 | Morse |

(List continued on next page.)

FOREIGN PATENT DOCUMENTS

| | | |
|---|---|---|
| AU | 699325 | 12/1998 |
| CA | 884608 | 11/1971 |
| DE | 196 40 451 A1 | 4/1998 |
| EP | 0 400 895 A1 | 12/1990 |
| EP | 0 117 613 B2 | 3/1993 |
| EP | 0 564 307 A1 | 10/1993 |
| EP | 0 612 233 B1 | 4/1996 |
| EP | 0 552 345 B1 | 9/1996 |
| EP | 0 516 964 B1 | 11/1996 |
| EP | 0 638 303 B1 | 11/1997 |
| EP | 0 652 736 B1 | 10/1998 |
| EP | 0 419 434 B2 | 11/1998 |
| EP | 0 758 220 B1 | 12/1998 |
| EP | 0 893 517 A2 | 1/1999 |
| WO | WO 83/03051 A1 | 9/1983 |
| WO | WO 92/07535 A1 | 5/1992 |
| WO | WO 93/21879 A1 | 11/1993 |
| WO | WO 95/24878 A1 | 9/1995 |
| WO | WO 97/19808 A1 | 6/1997 |
| WO | WO 97/24283 A1 | 7/1997 |
| WO | WO 98/22059 A1 | 5/1998 |
| WO | WO 98/24391 A2 | 6/1998 |
| WO | WO 98/43684 A1 | 10/1998 |
| WO | WO 99/00093 A1 | 1/1999 |
| ZA | 98/4033 | 5/1998 |

OTHER PUBLICATIONS

AATCC Test Method 127–1977, "Water Resistance: Hydrostatic Pressure Test," Technical Manual of the American Association of Textile Chemists and Colorists, reaffirmed 1977, p. 242.

(List continued on next page.)

Primary Examiner—Weilun Lo
Assistant Examiner—Michele Kidwell
(74) Attorney, Agent, or Firm—Pauley Petersen & Erickson

(57) ABSTRACT

An absorbent article is disclosed comprising a unitary absorbent layer having a central portion and an outer portion divided in part but not completely separated by one or more slits along a boundary surrounding the outer portion, further comprising a wicking barrier along at least a portion of the boundary. The central portion and outer portion of the unitary absorbent layer remain contiguous across one or more joining zones. A central rising member can be disposed beneath the central portion of the unitary absorbent layer to urge the central portion toward the body of the user when compressed laterally inward. The article is able to achieve good center-fill performance when in use and maintain excellent body fit.

79 Claims, 13 Drawing Sheets

U.S. PATENT DOCUMENTS

| | | |
|---|---|---|
| 3,575,174 A | 4/1971 | Mogor |
| 3,667,466 A | 6/1972 | Ralph |
| 3,860,003 A | 1/1975 | Buell |
| 3,881,489 A | 5/1975 | Hartwell |
| 3,881,491 A | 5/1975 | Whyte |
| 3,921,232 A | 11/1975 | Whyte |
| 3,989,867 A | 11/1976 | Sisson |
| 4,015,604 A | 4/1977 | Csillag |
| 4,100,324 A | 7/1978 | Anderson et al. |
| 4,195,634 A | 4/1980 | DiSalvo et al. |
| 4,247,362 A | 1/1981 | Williams |
| 4,285,343 A | 8/1981 | McNair |
| 4,324,246 A | 4/1982 | Mullane et al. |
| 4,342,314 A | 8/1982 | Radel et al. |
| 4,397,644 A | 8/1983 | Matthews et al. |
| 4,405,326 A | 9/1983 | Lenaghan |
| 4,421,812 A | 12/1983 | Plant |
| 4,425,130 A | 1/1984 | DesMarais |
| 4,463,045 A | 7/1984 | Ahr et al. |
| 4,476,180 A | 10/1984 | Wnuk |
| 4,480,516 A | 11/1984 | Leroy |
| 4,490,147 A | 12/1984 | Pierce et al. |
| 4,496,359 A | 1/1985 | Pigneul |
| 4,536,181 A | 8/1985 | Cook |
| 4,556,146 A | 12/1985 | Swanson et al. |
| 4,556,560 A | 12/1985 | Buckingham |
| 4,573,986 A | 3/1986 | Minetola et al. |
| 4,576,596 A | 3/1986 | Jackson et al. |
| 4,576,597 A | 3/1986 | Hlaban |
| 4,578,070 A | 3/1986 | Holtman |
| 4,589,876 A | 5/1986 | Van Tilburg |
| 4,608,047 A | 8/1986 | Mattingly |
| 4,654,040 A | 3/1987 | Luceri |
| 4,655,759 A | 4/1987 | Romans-Hess et al. |
| 4,662,876 A | 5/1987 | Wiegner |
| 4,687,478 A | 8/1987 | Van Tillburg |
| 4,701,177 A | 10/1987 | Ellis et al. |
| RE32,649 E | 4/1988 | Brandt et al. |
| 4,738,677 A | 4/1988 | Foreman |
| 4,753,644 A | 6/1988 | Cottenden et al. |
| 4,758,240 A | 7/1988 | Glassman |
| 4,804,380 A | 2/1989 | Lassen et al. |
| 4,846,824 A | 7/1989 | Lassen et al. |
| 4,879,170 A | 11/1989 | Radwanski et al. |
| 4,886,513 A | 12/1989 | Mason, Jr. et al. |
| 4,936,839 A | 6/1990 | Molee et al. |
| 4,950,264 A | 8/1990 | Osborn, III |
| 4,961,736 A | 10/1990 | McCloud |
| 4,964,857 A | 10/1990 | Osborn |
| 4,973,325 A * | 11/1990 | Sherrod et al. ............. 604/368 |
| 5,007,906 A | 4/1991 | Osborn, III et al. |
| 5,009,653 A | 4/1991 | Osborn, III |
| 5,030,314 A | 7/1991 | Lang |
| 5,147,343 A | 9/1992 | Kellenberger |
| 5,147,345 A | 9/1992 | Young et al. |
| 5,151,092 A | 9/1992 | Buell et al. |
| 5,188,625 A | 2/1993 | Van Iten et al. |
| 5,217,445 A | 6/1993 | Young et al. |
| 5,217,447 A | 6/1993 | Gagnon |
| 5,219,342 A | 6/1993 | Hatch et al. |
| 5,235,515 A | 8/1993 | Ungpiyakul et al. |
| 5,236,428 A | 8/1993 | Zajaczkowski |
| 5,267,992 A | 12/1993 | Van Tilburg |
| 5,300,055 A | 4/1994 | Buell |
| 5,308,346 A | 5/1994 | Sneller et al. |
| 5,324,278 A | 6/1994 | Visscher et al. |
| 5,324,575 A | 6/1994 | Sultze et al. |
| 5,342,337 A | 8/1994 | Runeman et al. |
| 5,342,342 A | 8/1994 | Kitaoka |
| 5,350,624 A | 9/1994 | Georger et al. |
| 5,354,400 A | 10/1994 | Lavash et al. |
| 5,360,420 A | 11/1994 | Cook et al. |
| 5,389,094 A | 2/1995 | Lavash et al. |
| 5,399,175 A | 3/1995 | Glaug et al. |
| 5,399,412 A | 3/1995 | Sudall et al. |
| 5,401,267 A | 3/1995 | Couture-Dorschner et al. |
| 5,413,568 A | 5/1995 | Roach et al. |
| 5,415,643 A | 5/1995 | Kolb |
| 5,429,628 A | 7/1995 | Trinh et al. |
| 5,429,629 A | 7/1995 | Latimer et al. |
| 5,429,630 A | 7/1995 | Beal et al. |
| 5,445,628 A | 8/1995 | Gipson et al. |
| 5,447,507 A | 9/1995 | Yamamoto |
| 5,462,166 A | 10/1995 | Minton et al. |
| 5,476,457 A | 12/1995 | Roessler et al. |
| 5,487,736 A | 1/1996 | Van Phan |
| 5,489,283 A | 2/1996 | Van Tillburg |
| 5,506,035 A | 4/1996 | Van Phan et al. |
| 5,514,104 A | 5/1996 | Cole et al. |
| 5,518,801 A | 5/1996 | Chappell et al. |
| 5,520,674 A | 5/1996 | Lavon et al. |
| 5,533,991 A | 7/1996 | Kirby et al. |
| 5,542,941 A | 8/1996 | Morita |
| 5,545,156 A | 8/1996 | DiPalma et al. |
| 5,547,745 A | 8/1996 | Hansen et al. |
| 5,562,645 A | 10/1996 | Tanzer et al. |
| 5,562,650 A | 10/1996 | Everett et al. |
| 5,567,260 A | 10/1996 | McFall |
| 5,575,785 A | 11/1996 | Gryskiewicz et al. |
| 5,591,146 A | 1/1997 | Hasse |
| 5,591,148 A | 1/1997 | McFall et al. |
| 5,591,150 A | 1/1997 | Olsen et al. |
| 5,599,339 A | 2/1997 | Horney |
| 5,601,544 A | 2/1997 | Glaug et al. |
| 5,611,790 A | 3/1997 | Osborn, III et al. |
| 5,618,282 A | 4/1997 | Schlangen |
| 5,620,430 A | 4/1997 | Bamber |
| 5,624,423 A | 4/1997 | Anjur et al. |
| 5,649,917 A | 7/1997 | Roberts et al. |
| 5,672,248 A | 9/1997 | Wendt et al. |
| 5,692,939 A | 12/1997 | DesMarais |
| 5,693,411 A | 12/1997 | Hansen et al. |
| 5,702,378 A | 12/1997 | Widlund et al. |
| 5,704,928 A | 1/1998 | Morita et al. |
| 5,704,930 A | 1/1998 | Lavash et al. |
| 5,704,932 A | 1/1998 | Hibbard |
| 5,711,970 A | 1/1998 | Lau et al. |
| 5,720,738 A | 2/1998 | Clark |
| 5,725,821 A | 3/1998 | Gannon et al. |
| 5,746,729 A | 5/1998 | Wada et al. |
| 5,753,343 A | 5/1998 | Braun et al. |
| 5,766,213 A | 6/1998 | Hackman et al. |
| 5,769,834 A | 6/1998 | Reiter et al. |
| 5,772,967 A | 6/1998 | Wannlund et al. |
| 5,773,120 A | 6/1998 | Deka et al. |
| 5,779,860 A | 7/1998 | Hollenberg et al. |
| 5,795,921 A | 8/1998 | Dyer et al. |
| 5,800,417 A | 9/1998 | Goerg-Wood et al. |
| 5,817,079 A | 10/1998 | Bergquist et al. |
| 5,817,081 A | 10/1998 | LaVon et al. |
| 5,817,394 A | 10/1998 | Alikhan et al. |
| 5,820,616 A | 10/1998 | Horney |
| 5,824,004 A | 10/1998 | Osborn, III et al. |
| 5,846,230 A | 12/1998 | Osborn, III et al. |
| 5,851,648 A | 12/1998 | Stone et al. |
| 5,853,867 A | 12/1998 | Harada et al. |
| 5,858,011 A | 1/1999 | Brown et al. |
| 5,858,021 A | 1/1999 | Sun et al. |
| 5,865,824 A | 2/1999 | Chen et al. |
| 5,869,033 A | 2/1999 | Schulz |
| 5,874,070 A | 2/1999 | Trinh et al. |

| | | |
|---|---|---|
| 5,874,071 A | 2/1999 | Yu et al. |
| 5,876,393 A | 3/1999 | Ahr et al. |
| 5,910,137 A | 6/1999 | Clark et al. |
| 5,954,705 A | 9/1999 | Sawaki et al. |
| 5,957,909 A | 9/1999 | Hammons et al. |
| 5,990,377 A | 11/1999 | Chen et al. |

OTHER PUBLICATIONS

American Society for Testing Materials (ASTM) Designation: D 3574–91, "Standard Test Methods for Flexible Cellular Materials—Slab, Bonded, and Molded Urethane Foams," pp. 303–319, published Mar. 1992.

American Society for Testing Materials (ASTM) Designation: D 4032–82, "Standard Test Method for Stiffness of Fabric by the Circular Bend Procedure," pp. 702–706, published Aug. 1982.

Federal Specification UU–T–595b, "Towel, Wiping, Paper: Industrial And Institutional," Apr. 4, 1967, 8 pages.

Federal Specification UU–T–595c, "Towel, Wiping, Paper: Industrial And Institutional," Jul. 27, 1976, 8 pages.

Gibson, P.W. et al., "Electrospun Fiber Mats: Transport Properties," AIChE Journal, vol. 45, No. 1, Jan. 1999, pp. 190–195.

Kim, S.H. et al., "Synthesis and Characterization of Dextran–Based Hydrogel Prepared By Photocrosslinking," Carbohydrate Polymers, vol. 40, No. 3, Sep. 1999, pp. 183–190.

Krema, Radko et al., "What's New In Highloft Production?" Nonwovens Industry, Oct. 1997, pp. 74–78.

Lee, Seungsin et al., "Antimicrobial and Blood Repellent Finishes for Cotton and Nonwoven Fabrics Based on Chitosan and Fluoropolymers," Textile Research Journal, 69(2), Feb. 1999, pp. 104–112.

Rahn, K. et al., "New Cellulosic Polymers By Subsequent Modification of 2,3–Dialdehyde Cellulose," Cellulose Chemistry and Technology, 32, 1998, pp. 173–183.

* cited by examiner

ABSORBENT ARTICLE WITH UNITARY ABSORBENT LAYER FOR CENTER FILL PERFORMANCE

BACKGROUND OF THE INVENTION

To prevent leakage of body exudates from absorbent articles such as feminine care pads or napkins and disposable diapers, it is desirable that the exudates not reach the edges of the absorbent material in the article. A "center fill" strategy is desirable for leakage control, wherein fluids are preferentially held in a central region of the article. Unfortunately, in traditional absorbent articles, there is generally no barrier to bulk flow or capillary wicking from the target region to the edges of the article, so leaking from the edges of the article is a persistent problem. Thus, in traditional articles, fluid entering the center of the article still has the potential to travel to the sides and leak. Flow from the center to the sides can be especially rapid when the article is compressed, bringing the wet central portion of the article in contact with absorbent material at the sides of the article.

The ability of an absorbent article to promote center fill and reduce leakage depends on the goodness of body fit achieved by the article in use. In sanitary napkins and other absorbent articles, the article as worn is often compressed laterally by the legs of the wearer, causing significant deformation of the article. In many conventional articles, the deformation is random or uncontrolled, resulting in a variety of product configurations that often may be inadequate for good uptake and fluid distribution in the article.

Past efforts to improve body fit and promote liquid uptake in the center of the article have included three-dimensional structures with elevated central members resting above the plane of a flat absorbent core. The elevated member can be a cylinder or an inverted U-shaped tube, for example. However, the elevated member adds substantially to the bulk of the article, potentially reducing comfort when worn and certainly decreasing packaging efficiency since fewer articles can fit into a package when the articles are no longer flat. Further, the article with an elevated central member can still suffer from leakage and smearing from fluid leaving the sides of the member.

Many other articles have been proposed for either improved body for or leakage protection which suffer from complexity of design and high cost, with multiple components comprising a variety of absorbent materials in the absorbent core.

What is needed is an article with good center fill performance that can reduce leakage to the sides of the article and provide good body fit with a simplified, low-cost absorbent core.

SUMMARY OF THE INVENTION

It has been discovered that a useful absorbent article with good leakage control can be produced with an absorbent core comprising a unitary absorbent layer and a thin, flexible wicking barrier, such as a polymeric film, which passes through the unitary absorbent layer along a portion of a boundary dividing the unitary absorbent layer into a central portion and an outer portion, wherein the two portions are nevertheless contiguous. The boundary comprises at least one slit and desirably two spaced apart slits through which the wicking barrier passes and further comprises a joining zone contiguously connecting the central portion with the outer portion. The interaction of the wicking barrier with the central and outer portions of the unitary absorbent layer results in an absorbent article having excellent leakage control and body fit. Further, the article offers a simple design in which a single piece of absorbent material forms the primary absorbent layer yet has multiple portions with fluid isolation therebetween provided by a wicking barrier. In a preferred embodiment, body fit is further enhanced by a deflection control element cooperatively associated with the central portion of the unitary absorbent layer.

As used herein, the term "unitary" means that all portions of a component are joined together without a physical discontinuity such as a gap or cut completely separating or severing one portion from another. Thus, a unitary object could be a single piece of a web provided with slits that do not completely sever the web into two or more pieces, or a single section of a laminated absorbent material with each ply bonded to adjacent plies. A section of web with a central cutout region that can be completely removed from the web without any need for tearing or cutting or disengaging entangled fibers is not unitary, even if the cutout section is placed back onto the web, for a physical discontinuity clearly has been created by the process of removing or cutting out one section.

Hence, in one aspect, the invention resides in an absorbent article for use on the body of a wearer, the absorbent article having two longitudinal sides, a target zone and a body side, the absorbent article comprising:

a) a liquid impervious backsheet;

b) a liquid pervious topsheet attached to the backsheet;

c) an absorbent core disposed between the topsheet and the backsheet comprising a unitary absorbent layer having a thickness, the unitary absorbent layer comprising a central portion and an outer portion separated in part by one or more slits passing through the thickness of the unitary absorbent layer and further comprising a boundary between the outer portion and the central portion; and d) a wicking barrier spanning a horizontal distance above the body-side surface of the outer portion of the unitary absorbent layer and spanning a vertical distance in the one or more slits of the unitary absorbent layer.

In another aspect, the invention resides in an absorbent article for use on the body of a wearer, the absorbent article having two longitudinal sides, a target zone and a body side, the absorbent article comprising:

a) a liquid impervious backsheet;

b) a liquid pervious topsheet attached to the backsheet;

c) a unitary absorbent layer disposed between the topsheet and the backsheet, the unitary absorbent layer having a thickness, and comprising a central portion and an outer portion separated by a boundary comprising a slit; and d) a wicking barrier spanning a horizontal distance on the surface of the outer portion of the unitary absorbent layer and spanning the thickness of the unitary absorbent layer in a portion of the slit.

In another aspect, the invention resides in a method of making an absorbent article having a body-side comprising:

a) providing a layer of absorbent material;

b) slitting a portion of the layer of absorbent member to define a central portion and an outer portion of the absorbent layer with a boundary separating the central portion from the outer portion, wherein the boundary comprises at least one slit and a joining zone between ends of the at least one slit, the joining zone connecting the outer portion to the central portion;

c) providing a first section of wicking barrier material along a portion of the boundary between the central portion and the outer portion of the layer of absorbent material, wherein the wicking barrier material spans a vertical distance in the layer of absorbent material;

d) providing a second section of wicking barrier material on or above the body-side surface of the outer portion of the layer of absorbent material;

e) sandwiching the layer of absorbent material a topsheet and a backsheet to form an absorbent article.

In still another aspect, the invention resides in a method of making an absorbent article having a body-side comprising:

a) providing a unitary layer of absorbent material;

b) providing the unitary layer of absorbent member with at least one slit that forms a longitudinal boundary dividing the longitudinal sides of a central portion of the unitary layer from an outer portion of the unitary layer;

c) inserting a segment of wicking barrier material through a portion of the slit to form a vertical wicking barrier between part of the central portion of the unitary layer and the outer portion of the unitary layer;

d) further providing a horizontal component of a wicking barrier above the body-side surface of the unitary layer to form a composite of a unitary layer and one or more wicking barrier materials;

e) disposing the composite above a backsheet;

f) disposing a topsheet above the composite;

g) attaching the topsheet to the backsheet.

The central portion of the unitary absorbent layer is adapted to receive fluid flow from the body of the wearer or from other fluid sources. Leakage from the longitudinal sides of the article is reduced or prevented by the wicking barrier between the central portion and the outer portion of the article in the target zone (e.g., the crotch region).

The wicking barrier spans a vertical distance in the absorbent core to effectively impede laterally outward flow from the central portion to the outer portion in the target zone. For best results, the wicking barrier extends vertically at least the thickness of the absorbent core, though it can also extend vertically a fraction of the thickness of the core (e.g., 50% or greater). The wicking barrier can be a film or strip of barrier material that has been inserted into one or more slits to span a vertical distance in the absorbent core and desirably to also span a horizontal distance on the body-side surface of the absorbent core, and preferably on the body-side surface of the outer portion thereof. In one preferred embodiment, the barrier material covers a substantial portion of the body-side surface of the outer portion of the absorbent core in the target zone and between the longitudinal sides of the absorbent article and the central portion of the unitary absorbent layer, then descends into spaced apart slits on the boundary around the central portion, and passes beneath at least a portion of the central portion along the garment-side surface of the unitary absorbent layer. The wicking barrier can be provided with apertures in the region beneath the central portion of the unitary absorbent layer to permit some degree of fluid flow therethrough, particularly to permit fluid flow to an absorbent layer residing below the central portion of the unitary absorbent layer.

The wicking barrier is typically a separate component that is not integral with other components of the article. However, it can also comprise material from the backsheet or topsheet. Thus, in one embodiment, the wicking barrier is integral or unitary with the backsheet, and comprises an extended portion of the backsheet which wraps part of the outer portion of the unitary absorbent layer and penetrates through opposing slits in the unitary absorbent layer, separating the outer portion from the central portion of the unitary absorbent layer. Less desirably, the wicking barrier can comprise material from the topsheet that penetrates into the absorbent core to separate the central portion from the outer portion of the unitary absorbent layer, wherein when the topsheet material that penetrates into the core is rendered substantially liquid impervious by chemical treatment, impregnation of adhesive or thermoplastic material, heat sealing, or the like.

The central portion, being partially separated from the outer portion by the presence of slits and a wicking barrier, can also be adapted to deflect upward toward the body of the wearer during inwardly lateral compression of the absorbent article in the target zone. In several embodiments, the central portion is relatively free to deflect upward substantially independently of the deflection of the surrounding outer portion of the absorbent core. Desirably, the combinations of slits and a wicking barrier permit the central portion to conform to the body during use by virtue of upward deflection.

A single slit along the boundary may curve to circumscribe a portion of the central portion of the unitary absorbent layer. The boundary can also include two or more spaced apart slits. Generally, the boundary further comprises a linear region (e.g., an imaginary line or elongated zone) herein defined as the "joining zone" which joins the ends of the slit or slits and provides a continuous span of absorbent material from the central portion to the outer portion of the unitary absorbent layer. In an article with a front end and a back end and having longitudinal slits, the boundary includes the slits and a line joining the front ends of the slits and a line joining the back ends of the slits. In an article with a right side and a left side and having a pair of spaced apart, substantially transverse slits, the boundary includes the slits and the line joining the right ends of the slits and the line joining the left end of the slits. In other words, the boundary comprises one or more slits and one or more joining zones between the ends of the one or more slits, wherein the one or more joining zones contiguously join the central portion to the outer portion.

In one embodiment, two or more sides of a central portion of the unitary absorbent layer are circumscribed by one or more slits such that only a single substantially linear region (a single linear joining zone) joins the central portion to the outer portion of the unitary absorbent layer, wherein the linear region joining the two portions serves as a hinge zone that permits the central portion to be lifted away from the plane of the unitary absorbent layer except for the material in the hinge zone, such that a wicking barrier or other object can be readily placed underneath the central portion, and such that portions of the wicking barrier can extend across the body-side surface of the outer portion of the unitary absorbent layer in the target zone. The hinge zone can be impregnated with hydrophobic material to prevent wicking therethrough.

Many articles of the present invention are intended to be worn in the crotch of a wearer, and thus have crotch regions. However, the present invention can also be applied to other articles such as underarm pads or wound dressings where a crotch region may not exist. In such cases, the article will have a region where fluid intake is intended to occur, termed the "target region." The portion of the article including the longitudinal length of the target region and the full transverse width of the article normal to length of the target region is defined herein as the "target zone." For articles intended to be worn in the crotch, the terms "target zone" and "crotch region" are generally synonymous, whereas "target region" generally excludes the portions of the absorbent core near the longitudinal sides since the intended area for fluid intake is generally substantially central in the absorbent article.

Opportunities for improved body fit are especially great if a deflection control element is disposed beneath or within the absorbent core, and particularly beneath or within the central portion of the absorbent core, whereby the central portion is urged toward the body of the wearer during use of the article. The deflection control element can be selected from a variety of elements or structures designed to influence the compressed shape of the article when worn and to urge the central portion of the absorbent core toward the body of the wearer or, more generally, toward a source of liquid exudates.

The deflection control element may be any of the following or a combination thereof:

1. a central rising member which deflects upward when compressed from the sides;
2. a central inflatable member or other inflatable member;
3. a relatively narrow pledget of absorbent material which forces the overlying unitary absorbent layer to assume a convex upward shape predisposing the unitary absorbent layer to deflect upward during laterally inward compression in the target zone or crotch region; and
4. bending lines and specifically shaping lines which influence bending of the central portion of the unitary absorbent layer.

The absorbent article in general can comprise a central rising member or central inflatable member in or beneath the unitary absorbent layer and preferably beneath the central portion of the unitary absorbent layer. Central rising members, central inflatable members, and related structures are described more fully in commonly owned, copending application U.S. Ser. No. unknown, "Center Fill Absorbent Article with Central Rising Member", by Chen et al. and U.S. Ser. No. unknown, "Absorbent Article with Central Pledget and Deformation Control", by Chen et al., both filed on the same day as the present application.

The use of a central rising member or central inflatable member under a central portion of the unitary absorbent layer is particularly effective in combination with a wicking barrier. Desirably, a portion of the wicking barrier also resides on the body-side surface of the absorbent core, particularly on the body-side surface of the outer portion of the unitary absorbent layer in the target zone. The wicking barrier serves to prevent lateral wicking of fluid to the longitudinal sides of the article and, when provided with a horizontal component on the surface of the absorbent core, serves to prevent fluid communication between the central portion of the unitary absorbent layer and the outer portion thereof when the article is bunched together in use. The wicking barrier can also help control the geometry of the absorbent article when in use under dynamic conditions, permitting flexure or folding such that the central portion of the unitary absorbent layer is urged toward the body or such that the topsheet of the article effectively contacts the body.

Good body fit can be promoted by the central rising member disposed in or beneath the absorbent core, preferably beneath the central portion of the unitary absorbent layer, wherein the central rising member deflects upward upon lateral compression from the longitudinal sides of the article. The deflection of the central rising member in turn deflects the central portion of the unitary absorbent layer upward toward the body of the wearer for good body fit. In conjunction with a central rising member, a wicking barrier separating the central portion from the outer portion can also permit or promote a degree of independent motion or deflection of the central portion toward the body. Similar effects can be achieved with a central inflatable member which deflects the central portion of the unitary absorbent layer toward the body and increases the three-dimensional nature of the absorbent article in use for improved leakage control.

Proper deformation of the absorbent core during use can also be promoted by one or more shaping lines and/or one or more crease lines in the absorbent core. A crease line, when used, generally lies along the boundary of the outer portion of the unitary absorbent layer or away from the central portion and promotes downward folding or bending of the article along the crease line (e.g., a valley fold) during lateral compression from the longitudinal sides of the article. A shaping line promotes upward folding or bending (e.g., a mountain fold) during lateral compression from the longitudinal sides of the article. A shaping line, if present, generally resides along or near the longitudinal centerline and typically will be primarily contained in the central portion of the unitary absorbent layer. A shaping line desirably coupled with at least two crease lines works to establish a W-fold geometry in the article when laterally compressed, offering good control over the upward deflection of the central portion in the absorbent core. Crease lines and shaping lines, as defined therein, will be generally referred to hereafter as "bending lines." Bending lines can be formed by one of more treatment methods such as embossing, stamping, or other known methods for creating densified regions, as described in U.S. Pat. No. 4,655,759, issued Apr. 7, 1987 to A. Y. Romans-Hess et al. Other methods for line formation include slitting; cutting; notching; tearing; thermobonding (application of heat to create bonding, particularly with thermoplastic materials or heat-setting resins); hot pressing (simultaneous application of heat and pressure, especially in conjunction with thermoplastic binder materials, thermosetting plastics, or heat setting resins); ultrasonic bonding; perforating; perf-embossing; needling; impregnation by resins, waxes, or thermoplastics; hydraulic cutting by water jets or other fluid jets; pre-folding; creasing; scoring; or removing material by abrasion, ablation, picking, scraping, or suction.

In certain embodiments, then, the crease lines and shaping lines may be a series of perforations, notches, cuts, tears, or slits optionally having portions not fully perforated, notched, cut, torn, or slit along a line's length for increased integrity. Crease lines and shaping lines formed by slitting or creation of densified areas are believed to be especially useful due to their ease of application and general effectiveness.

The length spanned by the shaping line or lines in the longitudinal direction can be at least about 1 cm, specifically at least about 2 cm, more specifically from about 3 cm to about 10 cm, more specifically still from about 4 cm to about 8 cm, and most specifically from about 4 cm to about 6 cm. In sanitary napkins and other absorbent articles, a longitudinal slit or notch, if present, desirably can be from about 4 cm to about 6 cm long. The longitudinal length of the crease lines can be smaller than that of the shaping lines, but in most embodiments desirably is about the same as or longer than that of the shaping line. For example, the crease lines can be longer than the shaping lines in the longitudinal direction by at least about 1 cm, more specifically at least about 2 cm, more specifically at least about 3 cm, and most specifically from about 2.5 cm to 5 cm.

In one embodiment, the central rising member can be a resilient material folded or rolled into the shape of the letter "e" such that lateral compression from the sides causes the upper section of the folded shape to deflect upwards. Other configurations can achieve the same purpose. The central rising member generally has flexure points or folded sections, such as is found in an "e"-folded web, such that lateral compression from the longitudinal sides of the central rising member causes at least a portion of the central rising member to deflect upwards with sufficient force that an overlying central absorbent member can be deflected toward the body (or that the central rising member itself can rise toward the body when it serves as the central absorbent member). An absorbent central rising member can also be configured as a flattened tube or an equivalent. Other shapes can also be effective, such as a layer of absorbent material folded or held in the shape of the letter "C" rotated 90 degrees to the right, similar to an inverted "U" with the ends brought together. The rotated "C" shape is especially useful when the internal void space therein is partially filled with another section of absorbent material to prevent collapse and to help predispose the shape to flex upward during lateral compression.

Possible uses of the present invention include absorbent articles for intake, distribution, and retention of human body fluids. Examples include feminine care pads and related catamenial devices or sanitary napkins, including "ultra-thin" pads and pantiliners and maxipads. Likewise, the present invention can be applied to diapers, disposable training pants, other disposable garments such as swimming garments, incontinence articles, bed pads, bandages, wound dressings, and other absorbent articles.

For feminine care pads in particular, the present invention offers surprising advantages. The presence of one or more slits in the boundary between the central portion and the outer portion of the unitary absorbent layer, coupled with the presence of a wicking barrier, can reduce stiffness of the article, reduce leakage of fluid toward the sides of the article, improve the ability of the central portion to conform to the body, reduce fluid flow on the surface of the article, and improve opportunities for controlled deformation of the article when worn. The presence of a wicking barrier with a vertical component in the target zone frequently appears useful in promoting a W-shape geometry of sanitary napkins when compressed in use which can rise toward the body for better intake of fluid and better fit in general. Further still, the center-fill strategy made possible by the present invention can be used to generally ensure that the outer portion remains relatively dry under typical usage conditions, which in turn allows the outer portion of the unitary absorbent layer to better maintain its shape and to help hold the pad in a comfortable and effective position, even as the central portion of the unitary absorbent layer receives a substantial quantity of fluid to absorb.

Definitions

As used herein, a material is said to be "absorbent" if it can retain an amount of water equal to at least 100% of its dry weight as measured by the test for Intrinsic Absorbent Capacity given below (i.e., the material has an Intrinsic Absorbent Capacity of at about 1 or greater). Desirably, the absorbent materials used in the absorbent members of the present invention have an Intrinsic Absorbent Capacity of about 2 or greater, more specifically about 4 or greater, more specifically still about 7 or greater, and more specifically still about 10 or greater, with exemplary ranges of from about 3 to about 30 or from about 4 to about 25 or from about 12 to about 40.

As used herein, "bulk" and "density," unless otherwise specified, are based on an oven-dry mass of a sample and a thickness measurement made at a load of 0.34 kPa (0.05 psi) with a 7.62-cm (three-inch) diameter circular platen. Thickness measurements of samples are made in a TAPPI-conditioned room (50% relative humidity and 23° C.) after conditioning for at least four hours. Samples should be essentially flat and uniform under the area of the contacting platen. Bulk is expressed as volume per mass of fiber in cc/g and density is the inverse, g/cc.

As used herein, the term "cellulosic" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose.

As used herein, the "crotch region" of an absorbent article refers to the generally central region that will be in contact with the crotch of the user, near the lowermost part of the torso, and resides between the front and rear portions of the article. Typically the crotch region contains the transverse centerline of the article and generally spans approximately 7 to 10 cm in the longitudinal direction.

As used herein, the term "extensible" refers to articles that can increase in at least one of their dimensions in the x-y plane by at least 10% and desirably at least 20%. The x-y plane is a plane generally parallel to the faces of the article. The term extensible includes articles that are stretchable and elastically stretchable (defined below). In the case of a sanitary napkin comprising an absorbent core, for example, the article and the absorbent core are desirably extensible both in length and width. The absorbent article, however, may only be extensible in one of these directions. Preferably, the article is extensible at least in the longitudinal direction. Examples of extensible materials and articles, and their methods of preparation, are disclosed in U.S. Pat. No. 5,611,790, issued Mar. 18, 1997 to Osborn III, herein incorporated by reference in its entirety.

As used herein, the term "flexure-resistant" refers to an element which will support a bending moment, in contrast to an element which will support only axial forces. Likewise, as used herein, "flexure resistance" is a means of expressing the flexibility of a material or article and is measured according to the Circular Bend Procedure described in detail in U.S. Pat. No. 5,624,423, issued Apr. 29, 1997 to Anjur et al., herein incorporated by reference in its entirety. Flexure resistance is actually a measurement of peak bending stiffness modeled after the ASTM D4032-82 Circular Bend Procedure. The Circular Bend Procedure of Anjur et al. is a simultaneous multidirectional deformation of a material in which one face of a specimen becomes concave and the other face becomes convex. The Circular Bend Procedure gives a force value related to flexure-resistance, simultaneously averaging stiffness in all directions. For comfort, the absorbent article desirably has a flexure-resistance of less than or equal to about 1,500 grams, more specifically about 1000 grams or less, more specifically still about 700 grams or less and most specifically about 600 grams or less. For shaping performance, the unitary absorbent layer can have a flexure resistance of at least about 30 grams, more specifically at least about 50 grams, and most specifically at least about 150 grams.

As used herein, the term "horizontal," refers to directions in the plane of the article that are substantially parallel to the body-side surface of the article, or, equivalently, substantially normal to the vertical direction of the article, and comprises the transverse direction and the longitudinal direction of the article, as well as intermediate directions.

As used herein, the term "hydrophobic" refers to a material having a contact angle of water in air of at least 90 degrees. In contrast, as used herein, the term "hydrophilic" refers to a material having a contact angle of water in air of less than 90 degrees.

As used herein, "hydrostatically liquid resistant" refers to material having a hydrostatic head of at least about 25 centimeters as determined in accordance with the standard hydrostatic pressure test AATCCTM No.127-1977 with the following exceptions: (1) The samples are larger than usual and are mounted in a stretching frame that clamps onto the cross-machine direction ends of the sample, such that the samples may be tested under a variety of stretch conditions (e.g., 10%, 20%, 30%, 40% stretch); and (2) The samples are supported underneath by a wire mesh to prevent the sample from sagging under the weight of the column of water.

As used herein "liquid resistant" refers to the property of a material which impedes the transport of liquids through and past such material and is inclusive of liquid impervious materials.

As used herein, the term "polymeric web" refers to a porous or nonporous layer primarily composed of polymeric material, and can be a nonwoven web, a plastic film, a polymeric film, an apertured film, or a layer of foam. Polymeric webs can be used as wicking barriers, baffle layers, backsheets, and, if sufficiently liquid pervious, as topsheets of absorbent articles. A polymeric web can consist of about 50 weight percent or more polymeric material, more specifically about 80 weight percent or more polymeric material, and most specifically about 90 weight percent or more polymeric material. Exemplary materials include polyolefins, polyesters, polyvinyl compounds, and polyamides.

As used herein, the term "transverse" refers to a line, axis, or direction which lies within the plane of the absorbent article and is generally perpendicular to the longitudinal direction. The z-direction is generally orthogonal to both the longitudinal and transverse centerlines. The term "lateral" refers to substantially in-plane directions having a predominately transverse component. Likewise, "inwardly lateral compression" refers to compression directed from the longitudinal sides of an article toward the longitudinal centerline thereof, applied substantially in the transverse direction.

The absorbent article comprising an absorbent core can, in addition to being extensible, also be stretchable. The term "stretchable", as used herein, refers to articles that are extensible when stretching forces are applied to the article and offer some resistance to stretching. The terms "elastically stretchable" or "elastically extensible" are intended to be synonymous. These terms, as used herein, mean that when in-plane stretching forces are removed, the article or absorbent fibrous structure will tend to return toward its unextended or unstretched dimensions (or original dimensions). It need not return all the way to its unstretched dimensions, however. It may return to relaxed dimensions between its unstretched dimensions and extended (or stretched dimensions).

In preferred embodiments wherein the central portion of the unitary absorbent layer is deflected upward toward the body during lateral compression, the degree of elevation of the central portion of the unitary absorbent layer can be quantified in terms of a Vertical Deformation test. As used herein, "Vertical Deformation" refers to the height increase experienced by the body-side surface of an absorbent article when the longitudinal sides in the crotch reason are gripped and steadily moved inward toward the longitudinal axis of the article, decreasing the span between the longitudinal sides by 1.5 cm. The Vertical Deformation test apparatus comprises two clamps having a clamp width (longitudinal length of the clamped portion of the edge of the article) of 5 cm. One clamp is stationary and the other is on a track that permits the clamp to slide to increase or decrease the distance between the clamps while keeping the clamp aligned and parallel to the other clamp. The clamps should be tilted downward at an angle of 20 degrees relative to horizontal, such that both outer edges of the absorbent article are slightly elevated relative to the nearest crease line, thus somewhat simulating the positioning of the outward edges of the absorbent article that may be induced by panties with elevated elastic edges in the target zone. The clamps are 5 cm above the surface of the track, permitting a pad to be suspended in air between the clamps, gripped in the crotch area such that a portion of the longitudinal sides of the absorbent core are held, with the clamps extending inward no more than about 3 mm from the outer edge of the absorbent core. The article should be held substantially taut in the region between the clamps without damaging the article, such that the target zone is substantially horizontal before lateral compression begins. At a rate of about 0.5 centimeters per second (cm/s), the slidable clamp is moved smoothly toward the fixed clamp by a distance of 50% of the initial width of the article in the target zone (or less if the article become incompressible such that more than about 5 kg of force is required to further compress the article). The height of the center of the pad or absorbent article is recorded before the clamp is moved and after the clamp is moved, yielding a difference that is reported as the Vertical Deformation. An increase in height is reported as a positive number, while a decrease is reported as a negative number. Desirably, the Vertical Deformation of the absorbent article is at least about 0.5 cm. Specifically, the Vertical Deformation is at least about 1 cm, and more specifically is at least about 1.5 cm and up to about 10 cm. Desirably, an absorbent article of the present invention exhibits an increase in Vertical Deformation in the target zone (specifically, the crotch region) of at least about 20%, and more specifically at least about 50%, relative to the Vertical Deformation in the target zone exhibited by an essentially identical absorbent article without a shaping line.

As used herein, "Central Elevation" is defined as the height difference between the center of the central portion of the unitary absorbent layer along the transverse centerline of the article and the average height of the longitudinal sides of the outer portion of the unitary absorbent layer along the transverse centerline of the article at the end of the Vertical Deformation Test as described above. The Central Elevation for absorbent articles of the present invention can be at least about 0.5 cm, specifically at least about 1 cm, and more specifically at least about 1.2 cm and up to about 10 cm. Desirably, an absorbent article of the present invention exhibits an increase in Central Elevation in the target zone of at least about 20%, and more specifically at least about 50%, relative to the Central Elevation in the target zone exhibited by an essentially identical absorbent article without a shaping line.

DETAILED DESCRIPTION OF THE DRAWINGS

Figure 1A:
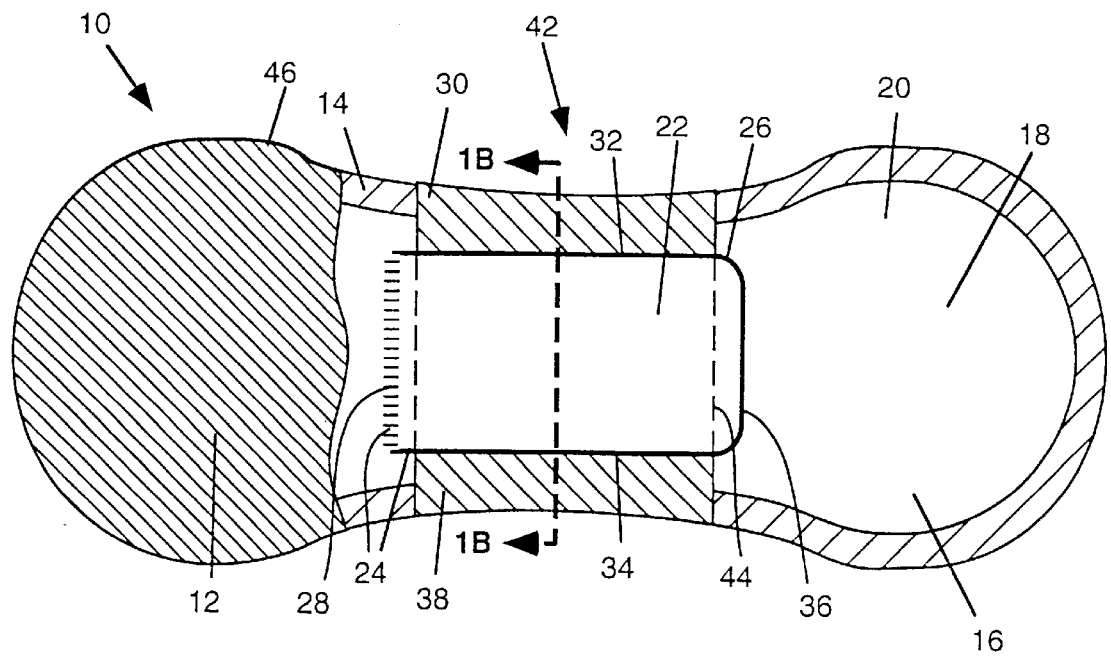
FIG. 1 depicts a top view and cross-sectional view of a sanitary napkin of the present invention having a central portion surrounded on three sides by a slit.

FIG. 1A depicts an absorbent article 10 of the present invention comprising a topsheet 12 that is partially cutaway to reveal other elements, a backsheet 14, and an absorbent core 16 comprising a unitary absorbent layer 18. The core 16 is disposed between the backsheet 14 and the topsheet 12, which are joined to each other at the periphery 46. The unitary absorbent layer 18 comprises an outer portion 20, a central portion 22, and a boundary 24 separating the outer portion 20 from the central portion 22, the boundary comprising a slit 26 and a joining zone 28. In this case the joining zone serves as a hinge zone (or hinge line) contiguously joining the central portion 22 to the outer portion 20. The article 10 also comprises a slit 26. The presence of the slit 26 and the joining zone 28 permits the central portion 22 to be lifted away from the remainder of the unitary absorbent layer 18 (assuming the absence of adhesive connecting the central portion 22 of the unitary absorbent layer 18 to underlying elements). The joining zone 28 (or hinge zone) can be impregnated with hydrophobic material to further reduce wicking away from the central portion.

The slit 26 comprises two substantially longitudinal slit components 32, 34 spaced apart about the longitudinal centerline of the article 10 to separate the longitudinal sides of the central portion 22 from the outer portion 20. The two substantially longitudinal slit components 32, 34 are joined at one end by a substantially transverse slit component 36. Thus, a rectangle fitting within the boundary 24 around the central portion 22 would have three sides of the rectangle blocked by the presence of the slit 26, meaning that any line extending outward in the plane of the article normal to any portion of one of the three blocked sides would intersect the slit 26, while a line extending outward from and normal to the fourth or unblocked side of the rectangle would encounter the joining zone 28 and not the slit 26. As depicted in FIG. 1A, the slit substantially has a U-shape (or horseshoe shape).

The wicking barrier 30 comprises a horizontal component 38 on the surface of the outer portion 20 in the crotch region 42, the horizontal component 38 extending from the boundary 24 of the central portion 22 toward the longitudinal sides of the article 10 by a distance desirably of at least 1 mm, specifically at least 2 mm, more specifically at least 4 mm, and most specifically from about 3 mm to about 10 mm. Suitably, the horizontal component 38 can extend the entire distance from the boundary of the central portion 22 to the longitudinal sides of the unitary absorbent layer 18 in the crotch region 42, and may further extend to wrap the sides of the outer portion 20 of the unitary absorbent layer 18 and can further extend to join with the backsheet 14 or form part of the backsheet 14, or the wicking barrier 30 can be an extension of the backsheet 14. The wicking barrier 30 may extend beneath the central portion 22 of the unitary absorbent layer 18 to define an underlying component 44.

The absorbent material of the unitary absorbent layer 18 can comprise cellulosic airlaid webs of comminuted fibers (commonly termed "airfelt"); cellulose-superabsorbent mixtures or composites; hydroentangled webs comprising cellulosic fibers; composites of synthetic fibers and papermaking fibers such as coform, as disclosed in U.S. Pat. No. 4,879,170, issued Nov. 7, 1989 to Radwanski et al.; rayon; lyocell or other solvent-spun hydrophilic fibers, such as those disclosed in U.S. Pat. No. 5,725,821, issued Mar. 10, 1998 to Gannon et al.; cellulosic foams including regenerated cellulose foams; hydrophilic, flexible foams or absorbent foams produced from high internal phase emulsions (HIPE), such as the foams disclosed in U.S. Pat. No. 5,692,939, issued Dec. 2, 1997 to DesMarais; fiber-foam composites; the foam-structured fibrous absorbent materials of F.-J. Chen et al. disclosed in the commonly owned, copending U.S. patent application "Fibrous Absorbent Material and Methods of Making the Same," Ser. No. 09/083,873, filed May 22, 1998; absorbent nonwoven webs; cotton; wool or keratin fibers; peat moss and other absorbent vegetable matter, and the like.

In one embodiment, at least one component of the absorbent core 16 comprises a molded, three-dimensional high bulk wet laid cellulosic web, such as an uncreped through-air dried web as taught by F.-J. Chen et al. in commonly owned U.S. patent application, Ser. No. 08/912,906, "Wet Resilient Webs and Disposable Articles Made Therewith," filed Aug. 15, 1997 or U.S. Pat. No. 5,399,412, issued to S. J. Sudall and S. A. Engel on Mar. 21, 1995. Such uncreped structures can offer a plurality of flow channels along the surface of the web. When stacked or layered with other planar materials such as a polymer film, void space can still exist adjacent the surface of the tissue web to permit rapid flow of fluid parallel to the plane of the tissue web. Further, the uncreped tissues show excellent wet resiliency and high bulk under load when wet.

Useful sources of cellulosic fibers include wood fibers, such as bleached kraft softwood or hardwood, high-yield wood fibers, and chemithermomechanical pulp fibers; bagasse; milkweed; wheat straw; kenaf; hemp; pineapple leaf fibers; or peat moss. High-yield fibers such as BCTMP can be flash-dried and compressed into dense pads which expand substantially when wetted.

The unitary absorbent layer 18 desirably has a mean density less than 0.2 g/cc, specifically less than 0.15 g/cc, more specifically still between about 0.025 g/cc and about 0.15 g/cc, and most specifically between about 0.04 g/cc and about 0.12 g/cc.

Basis weights of the components of the absorbent core 16 can be adjusted and optimized for particular purposes over a wide range. Thus, the basis weight of the unitary absorbent layer 18 can range, for example, from about 100 grams per square meter (gsm) to about 2500 gsm, more specifically from about 200 gsm to about 1200 gsm, and more specifically still from about 300 gsm to about 800 gsm. The ratio of the basis weight of the outer portion 20 to the basis weight of the central portion 22 can range from about 0.2 to about 3, for example. It is desirable in some embodiments that the outer portion 20 have a lower basis weight than the central portion 22, in which case the ratio of the basis weight of the outer portion 20 to the basis weight of the central portion 22 can range from about 0.2 to about 1, more specifically from about 0.3 to about 0.9, more specifically still from about 0.3 to about 0.7, and alternatively less than about 0.5.

The absorbent capacity of either the central portion 22 or the outer portion 20 of the unitary absorbent layer 18 can be optimized for the intended use of the article 10. In diapers, the absorbent capacity of the central portion 22 generally should be greater than about 60 ml and can be about 300 ml or less of fluid, more specifically about 200 ml or less, more specifically still about 150 ml or less, with exemplary ranges of from about 80 ml to about 250 ml or from about 100 ml to about 300 ml. For some uses, such as in sanitary napkins, it is desirable that the absorbent capacity of the central portion 22 of the unitary absorbent layer 18 be at least 7 ml of fluid, specifically at least 10 ml, more specifically at least 16 ml, more specifically still at least 20 ml, and most specifically from about 15 ml to about 35 ml. In one embodiment, the absorbent capacity of the outer portion 20 is less than the absorbent capacity of the central portion 22. For example, the outer portion 20 an have an absorbent capacity of about 5 to about 100% of the absorbent capacity of the central portion 22, or the ratio can be about 90% or less, more specifically about 70% or less, and more specifically still about 30% or less. If desired, however, the outer portion 20 can have a higher absorbent capacity than the central portion 22.

Superabsorbent particles can be placed in any portion of the absorbent core 16 to optimize performance of the article. Any known hydrogels or superabsorbent particles, including those in fibrous form, can be used. Superabsorbent particles attached to cellulosic or nonwoven fibers can be used. Further, dextran-based hydrogels and superabsorbent materials can be applied, including photocrosslinked materials as described by S. H. Kim and C. C. Chu, "Synthesis and Characterization of Dextran-Based Hydrogel Prepared by Photocrosslinking," *Carbohydrate Polymers*, Vol. 40, No. 3, Sep. 9, 1999, pp. 183–190.

For ultrathin pads and other absorbent articles, it is desirable that the dry components of the absorbent core 16 have a total thickness between about 2 mm and about 15 mm, and more specifically from about 3 mm to about 8 mm. When wetted, the central portion 22 and/or the outer portion 20 of the unitary absorbent layer 18 can increase substantially in thickness and void volume, such as a thickness increase of about 100% or greater, more specifically about 200% or greater, and more specifically still about 300% or greater. An example of a low-cost cellulosic component capable of increasing in thickness when wet is the absorbent material of Chen and Lindsay disclosed in commonly owned copending U.S. application Ser. No. 08/848,353, "Self-texturing Absorbent Structure and Absorbent Articles Made Therefrom," filed Apr. 21, 1997, or the densified structures of Hollenberg et al. in U.S. Pat. No. 5,779,860, "High-density Absorbent Structure," issued Jul. 14, 1998. Regenerated cellulose sponge materials are also capable of expanding significantly when wet and can be used to enhance body fit and conformability by providing nonuniform basis weights that expand in a three-dimensional shape. Densified cross-linked cellulosic mats can also be used for any absorbent member, as can crosslinked cellulosic fibers in general, and can include the webs and structures disclosed in any of the following patents: U.S. Pat. No. 5,360,420, issued Nov. 1, 1994 to Cook et al.; U.S. Pat. No. 5,324,575, issued Jun. 28, 1994 to Sultze et al.; and U.S. Pat. No. 5,217,445, issued Jun. 8, 1993 to Young et al.

Any portion of the absorbent core 16 or other absorbent members can embossed for improved control over fluid wicking, if desired. The absorbent members likewise may be apertured, slitted for improved flexibility and body conformability, perf-embossed, calendered, or pleated. The longitudinal sides and edges in general of the unitary absorbent layer may be treated with hydrophobic agents to prevent fluid flow, or may be encircled with a wall or barrier ring of hydrophobic fibers.

Other components (not shown) may be combined with the materials of the absorbent core 16 or added as separate layers or portions of the article. Such other components include odor absorbing components such as baking soda, talc powder, cyclodextrin, ethylenediamine tetra-acetic acid, zeolites, activated silica, and activated carbon granules, fabrics or fibers; superabsorbent particles and fibers; fluoropolymers; antimicrobial agents including the silver-loaded zeolites of BF Technologies, located in Beverly, Mass., sold under the trademark HEALTHSHIELD™, as well as triclosan products, chitosan or chitin derivatives (useful principles for application of chitosan finishes to nonwovenwebs and cellulosic fibers are described by S. Lee et al., "Antimicrobial and Blood Repellent Finishes for Cotton and Nonwoven Fabrics Based on Chitosan and Fluoropolymers," *Textile Research Journal*, 69(2): 104–112, February 1999, herein incorporated by reference); polycarboxylic acids; encapsulated perfumes; emollients such as lanolin; or skin wellness agents such as aloe vera extract (particularly aloe vera powder combined with a polyhydroxy softener) or vitamin E.

The unitary absorbent layer 18 generally can be of any shape such as circular, elliptical, rectangular, triangular, polygonal, dog-bone shaped, hourglass shaped, diamond shaped, or bicycle-seat shaped. The central portion 11 of the unitary absorbent layer 18 desirably has a longitudinal length greater than the width, with the length extending desirably across 30% or more of the length of the article, more specifically 50% or more, more specifically still 75% or more, and most specifically 90% or more of the length of the absorbent article 10. The maximum width of the central portion 22 desirably is no more than about 90% of the width of the absorbent article 10 in the target zone, more specifically no more than about 75%, and more specifically still no more than about 60% of the width of the absorbent article 10.

The unitary absorbent layer 18 can comprise between about 20% and 100% of the mass of the absorbent core 16 on a dry basis, more specifically between about 40% and 1000%, more specifically still between about 50% and 90%, and most specifically from about 60% to less than 90%.

The "edge width" of the outer portion of the unitary absorbent layer 18, defined herein as the lateral distance along a continuous portion of the outer portion 20 along the transverse centerline, specifically from the inner edge (adjacent the central portion) of the outer portion 20 to the outer edge thereof, is desirably at least about 2 mm and specifically at least about 3 mm, more specifically at least about 4 mm. For example, a 7 cm wide rectangular foam section with a 5 cm wide central portion 22 therein separated from the outer portion by thin longitudinal slits would have an edge width of about 1 cm.

The absorbent core 16 can further comprise fluid distribution elements such as the pumping elements of U.S. Pat. No. 5,769,834, issued Jun. 23, 1998 to Reiter et al., wherein tubular elements (not shown) are used to move fluid from one region of the absorbent core 16 to another. The tubular elements desirably are outside the central portion 22 of the absorbent core 16 and are adapted to intercept liquid that may escape from the longitudinal sides of the central portion 22 of the unitary absorbent layer 18 and move it toward the longitudinal ends of the absorbent core 16.

Figure 1B:
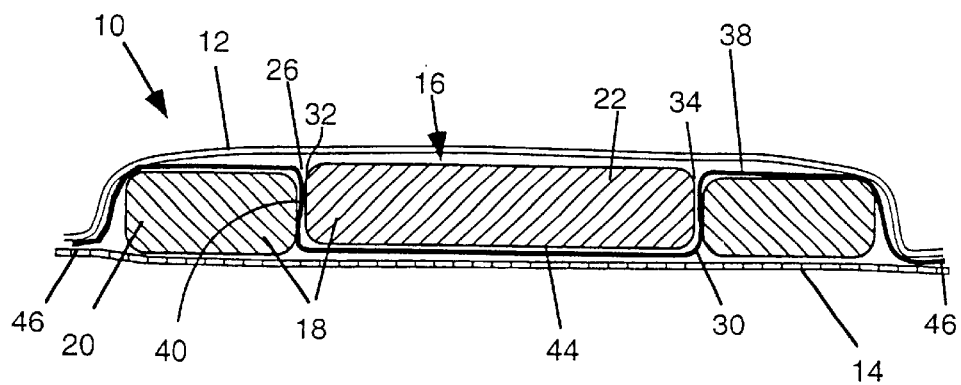

FIG. 1B provides a cross-sectional view of the absorbent article 10 from FIG. 1A. The view is taken along the transverse centerline. The unitary absorbent layer 18 is disposed between the topsheet 12 and the backsheet 14. The outer portion 20 of the unitary absorbent layer 18 is separated from the central portion 22 by longitudinal slit components 32, 34 and by a wicking barrier 30 passing through both of the longitudinal slit components 32, 34. The wicking barrier 30 has a horizontal component 38 on the body-side surface of the outer portion 20, a vertical component 40 spanning the entire thickness of the unitary absorbent layer 18 in the crotch region, a underlying portion 44 extending across the garment-side surface of the central portion 22 of the unitary absorbent layer 18 and joining the vertical components 40 of the wicking barrier 30 in the longitudinal slit components 32, 34 of the slit 26.

One or more optional tissue layers (not shown) may be disposed directly beneath the topsheet 12 to assist in fluid intake and suitably to restrain superabsorbent particles or other particles that may be present. Two sheets may be present with the uppermost tissue sheet having a bulk of from about 0.01 to about 0.1 grams per cubic centimeter (g/cc) and the second sheet having a higher density, such as from about 0.08 to about 0.3 g/cc, exemplified by the teachings of European Patent 652,736-B1, published Oct. 28, 1998.

The wicking barrier 30 can comprise an impermeable, flexible polymeric film, a meltblown film, an apertured film, a hydrophobically treated tissue, a nonwoven web, or other wicking inhibiting layer. It serves to hinder lateral flow from the sides of the central portion 22 of the unitary absorbent layer 18 to the sides, particularly the longitudinal sides, of the outer portion 20 of the unitary absorbent layer 18. The permeability, porosity or surface chemistry of the wicking barrier 30 can vary with position along the material of the wicking barrier 30 such that wicking is delayed or hindered to differing extents at different locations.

Beneath the central portion 22, an optional deflection control element such as a central rising member (not shown) or central inflatable member (not shown) can be disposed to further help control deflection and body fit of the article 10.

The outer surface of backsheet 14 can be coated with adhesive such as the pressure-sensitive adhesive strips (not shown) protected with release liners prior to use. The backsheet 14 is generally impermeable and may be breathable in whole or in zones, and may be stretchable or extensible.

The topsheet 12 is liquid permeable and, when the article 10 is in use, is in close proximity to the skin of the user. Desirably, the topsheet 12 is compliant, soft and nonirritating to the user's skin. It can be made from any of the conventional materials for this type of use. Nonlimiting examples of suitable materials include woven and nonwoven polyester, polypropylene, nylon, rayon or the like, particularly in the form of formed or apertured thermoplastic films, including those described in U.S. Pat. No. 4,324,246 issued to Mullane and Smith on Apr. 13, 1982 and U.S. Pat. No. 4,342,314 issued to Radel and Thompson on Aug. 3, 1982. Mechanically apertured forms can also be used. Other known topsheet materials can be employed, including those made from textured cellulosic basesheets with hydrophobic matter added to selected portions of the basesheet, particularly the most elevated portions of the basesheet, as described in commonly owned copending U.S. application, "Dual-zoned Absorbent Webs", Ser. No. 08/997,287, filed Dec. 22, 1997.

Figure 2:
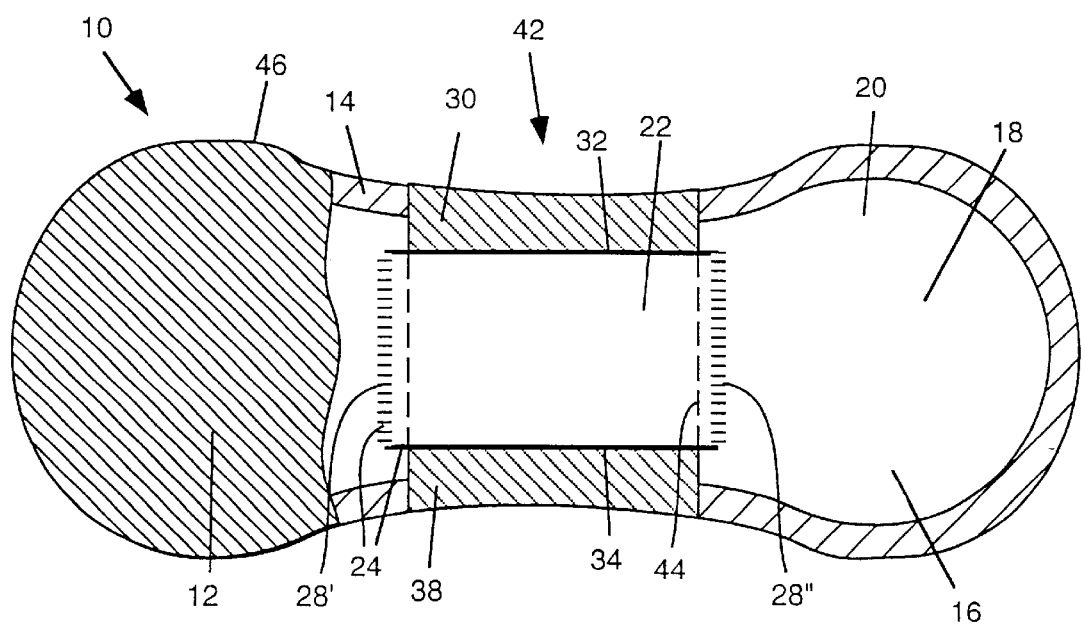
FIG. 2 depicts a top view of an article having two substantially longitudinal slits forming part of the boundary between a central portion and outer portion of a unitary absorbent layer.

FIG. 2 depicts the top view of an absorbent article 10 similar to that of FIG. 1A. The central portion 22 is separated from the outer portion 20 of the unitary absorbent layer 18 by two substantially longitudinal slit components 32, 34 which, in this case, are separate and not joined by a transverse slit component. The longitudinal slit components 32, 34 extend substantially across the length of the crotch region 42 and have a length greater than the length of the wicking barrier 30. The central portion 22 is surrounded by a boundary 24 comprising the two longitudinal slit components 32, 34 and two joining zones 28', 28" contiguously joining the central portion 22 of the unitary absorbent layer 18 to the outer portion 20 thereof. The joining zones 28', 28" can be further impregnated with hydrophobic material to prevent wicking toward the longitudinal ends of the article 10. The wicking barrier 30 has a horizontal component 38 above the body-side surface of the unitary absorbent layer 18, and particularly above the body-side surface of the outer portion 20 of the unitary absorbent layer 18 in the crotch region 42. As shown, the wicking barrier 30 extends from the longitudinal slit components 32, 34 to the backsheet 14, but can extend a shorter distance to cover a length of the outer portion 20 in the crotch region 42 without reaching to or extending past the longitudinal sides of the unitary absorbent layer 18.

Figure 3A:
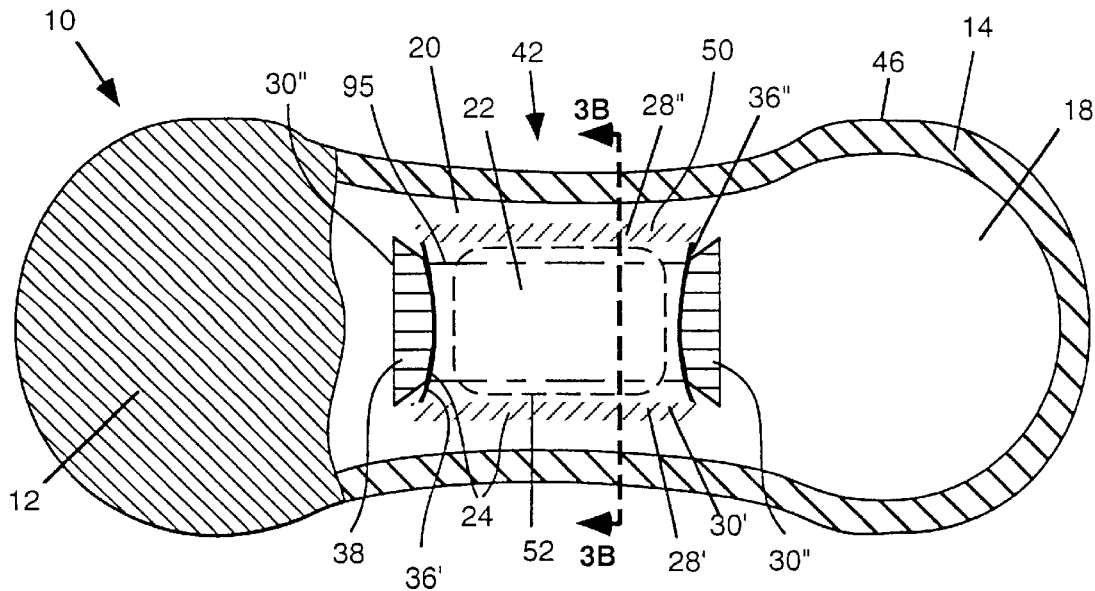
FIG. 3 depicts top view of a sanitary napkin of the present invention with two transverse slits separating the central portion from the outer portion of the unitary absorbent layer.
Figure 3B:
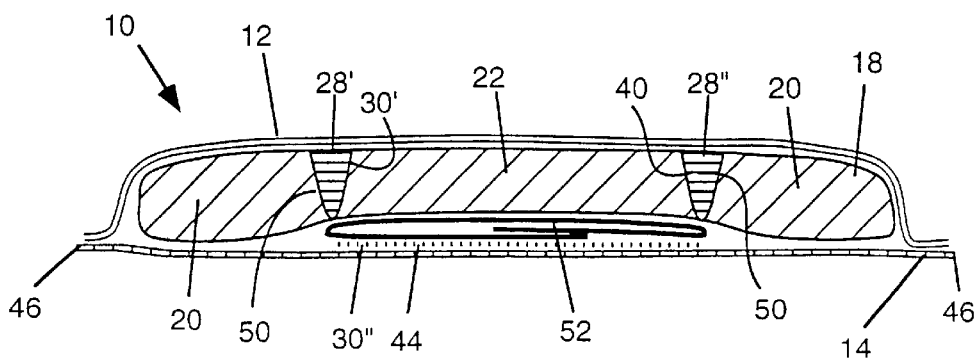

FIG. 3A depicts an article 10 according to the present invention shown from a top view. FIG. 3B depicts a cross-sectional view thereof. In FIGS. 3A and 3B, the unitary absorbent layer 18 of the article 10 comprises a an outer portion 20 separated from a central portion 22 by a boundary 24 comprising two substantially transverse slit components 36', 36" and two substantially longitudinal impregnated joining zones 28', 28" containing a hydrophobic impregnated material 50 that extends a vertical distance into the unitary absorbent layer 18. The joining zones 28', 28" serve as a wicking barrier, and particularly as a wicking barrier to transverse flow, having a vertical component 40 corresponding to the mean depth of penetration, which, as shown in FIG. 3B, can be substantially equal to the thickness of the unitary absorbent layer 18 in the crotch region 42 (i.e., the hydrophobic impregnated material 50 in the joining zones 28', 28" as depicted extends from the body-side surface of the unitary absorbent layer 18 to the garment-side surface thereof) or can extend across about 10% or more of the thickness of the unitary absorbent layer 18, more specifically about 30% or more, more specifically still from about 40% to about 90%, and most specifically from about 50% to 100%.

Beneath the central portion 22 of the unitary absorbent layer 18 is an optional deflection control element in the form of a central rising member 52, which, as depicted in FIG. 3B, can be an "e"-folded web of resilient material. Also extending beneath the central portion 22 is an optional second wicking barrier 30" to serve as barrier to longitudinal flow and which has a horizontal components 38 on the body-side surface of the outer portion 20 of the unitary absorbent layer 18, then passes vertically downward through the spaced apart transverse slit components 36', 36" to provide an underlying component 44 that extends beneath the central portion 22 of the unitary absorbent layer 18. The underlying component 44 of the second wicking barrier 30" is depicted in FIG. 3B as passing under the central rising member 52, which is generally desirable, but it can also pass over the central rising member 52.

Figure 4:
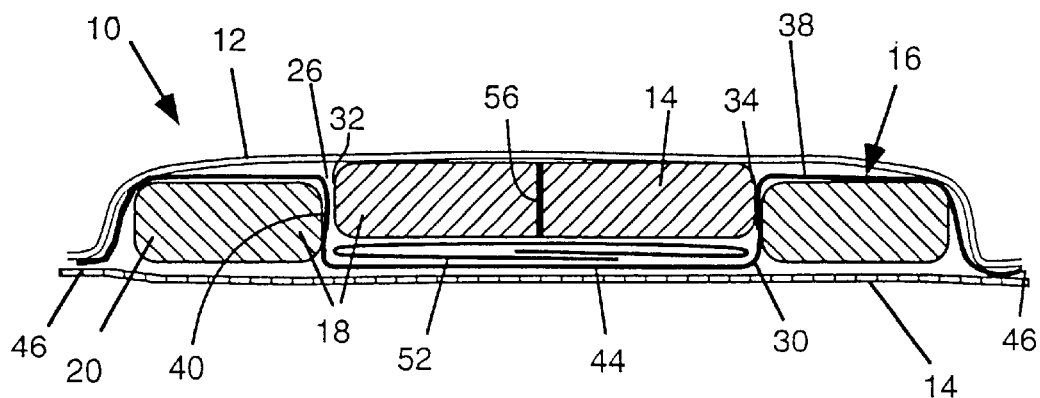
FIG. 4 depicts the article of FIG. 1 in a cross-sectional view with an additional central rising member beneath the central portion of the unitary absorbent layer and with a longitudinal slit in the central portion.

FIG. 4 depicts a variation of article 10 from FIG. 1 in a cross-sectional view, comprising an additional central rising member 52 beneath the central portion 22 of the unitary absorbent layer 18 and above the underlying portion 44 of the wicking barrier 30 and showing a longitudinal shaping line 56 in the central portion 22 to promote upward folding along the longitudinal centerline of the article 10 during lateral compression. The shaping line 52 can be a slit, as shown, or a scoremark that is a deformation or crease in the unitary absorbent layer 18 formed by a sharp upward fold made prior to assembling the article 10. Alternatively, the shaping line can be a notch created by removal of material in the central portion 22, wherein the notch penetrates at least about 20% of the layer thickness and preferably at least about 40% of the layer thickness.

The central rising member 52 depicted here alternatively could be replaced with other deflection control elements such as a central inflatable member (not shown), which could be an initially flat central pouch which inflates with gas when in use or just prior to use to deflect the central portion 22 of the unitary absorbent layer 18 toward the body of the wearer.

Figure 5:
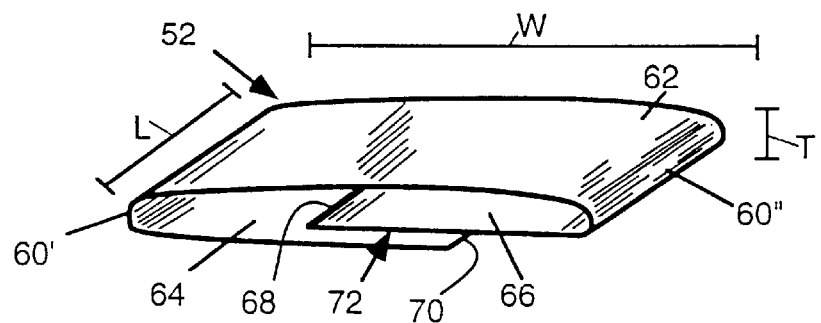
FIG. 5 is a perspective view of an "e"-folded web for use as a central rising member.

FIG. 5 shows a perspective view of the central rising member 52 which comprises a sheet of material that is folded or wrapped to have two longitudinal sides 60', 62", an upper portion 62, a first lower portion 64 and a second lower portion 66, each of which terminates respectively into ends 68, 70. The terminal portions of the lower portions 64, 66 overlap in an overlapping region 72. The two lower portions 68, 70 in the overlapping region 72 can be free to slide past each other or may be joined in a fixed relationship to prevent sliding of one lower portion relative to the other. In the embodiment shown, the lower portions 68, 70 are freely slidable relative to one another. The central rising member 52 has a transverse width W, a longitudinal length L, and a z-direction thickness T. Specifically, the width W of the central rising member 52 can be about 90% or less, more specifically about 70% or less, more specifically still about 50% or less of the minimum width of the absorbent core 16 in the crotch region or target zone of the absorbent article 10. Without limitation, dimensions of width W, thickness, T, and length L for a central rising member 52 suitable for a sanitary napkin and related absorbent articles can include the following, given for the article 10 in its unused, uncompressed state: for width W, from about 10 mm to about 60 mm, more specifically from about 15 mm to about 40 mm; for thickness T, from about 1 mm to about 15 mm, more specifically from about 3 mm to about 8 mm; for length L, from about 10 mm to about 100 mm, more specifically from about 15 mm to about 70 mm, and most specifically from about 20 mm to about 50 mm.

Preferably, the upper portion 62 of the "e"-folded central rising member 52 is toward the body side of the absorbent article 10 as shown in FIG. 4 (toward the topsheet 12) and the lower portions 68, 70 are toward the garment side of the article 10 in order to obtain the best deformation of the central rising member 52 toward the body side of the user when the article 10 is worn and compressed laterally inward.

Figure 6:
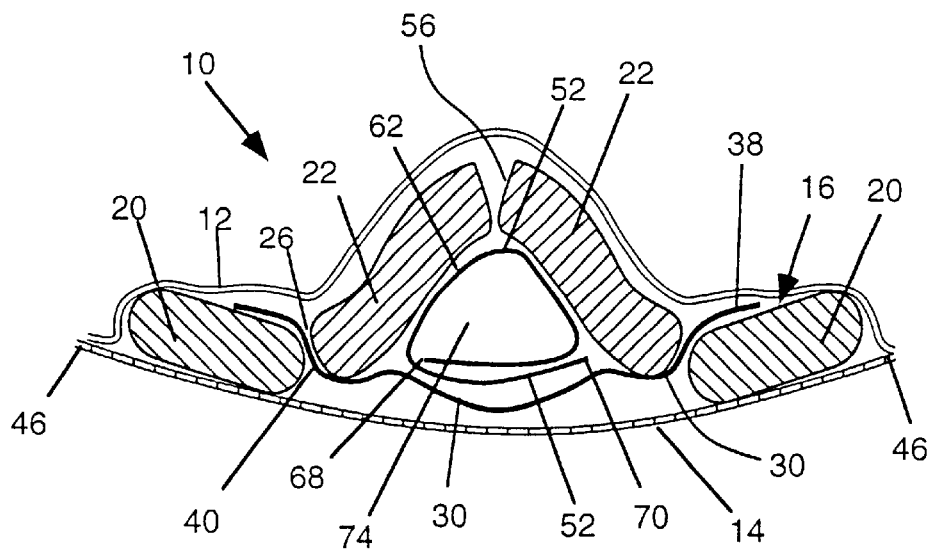
FIG. 6 depicts the article of FIG. 5 in a deformed state, with upward flexure of the central portion of the article caused by inwardly lateral compression.

FIG. 6 depicts the absorbent article 10 of FIG. 1 after lateral compression in which the central rising member 52 has deflected upward to urge the overlying central portion 22 of the unitary absorbent layer 18 toward the body. The ends 68, 70 of the central rising member 52 have moved toward opposing longitudinal sides thereof as the upper portion 62 has deflected upward, resulting in formation of a void space 74 beneath the central portion 22 and within the central rising member 52. At least along the transverse cross-section shown, and desirably generally in the crotch region, the central portion 22 is not in fluid communication with the outer portion 20 by virtue of the wicking barrier 30, and particularly the vertical component 40 which prevents fluid flow from the neighboring portions of the central portion 22 and the outer portion 20. The horizontal component 38 of the wicking barrier 30 on the body-side surface of the outer portion 20 of the unitary absorbent layer 18 also prevents fluid communication and surface smearing when the article 10 is momentarily severely deformed or compressed during the dynamic conditions of actual use. The optional shaping line 56 in the central portion 22 promotes establishment of a relatively sharp mountain fold substantially along the longitudinal centerline during lateral compression.

Figure 7:
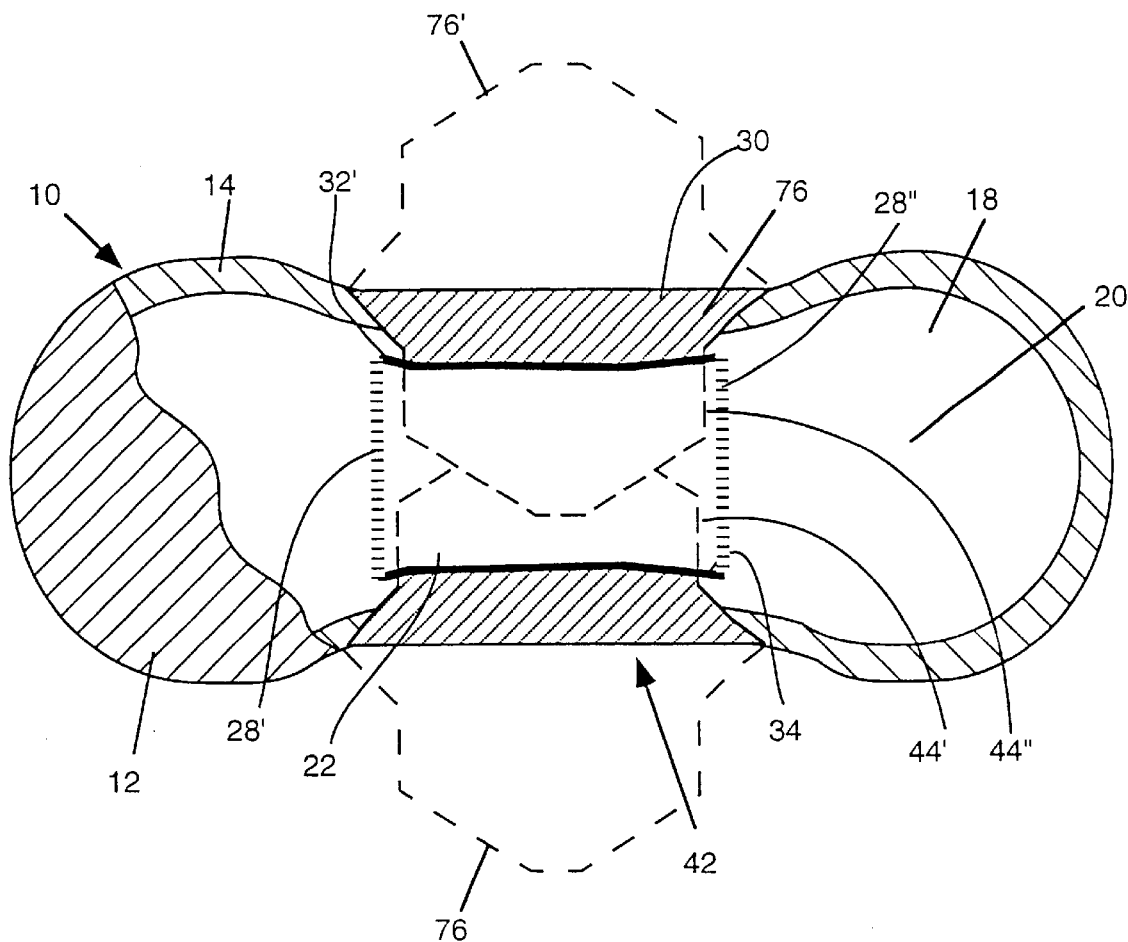
FIG. 7 depicts a top view of a sanitary napkin in which wing-like extensions of the backsheet wrap the body-side surface of the unitary absorbent layer in the target zone and descend into substantially longitudinal slits therein.

FIG. 7 depicts a top view of an absorbent article 10 (here, a sanitary napkin) in which wing-like extensions 76 of the backsheet 14 form a wicking barrier 30 as they wrap the body-side surface of the unitary absorbent layer 18 in the crotch region 42 and descend into substantially longitudinal slit components 32, 34 therein. The longitudinal slit components 32, 34 define the longitudinal boundaries of a central portion 22 of the unitary absorbent layer 18, the central portion 22 being surrounded by the outer portion 20. Linear contiguous joining zones 28', 28" span the ends of the longitudinal slit components 32, 34. The width of the joining zones 28', 28" can generally be about 0.3 mm or greater, more specifically from about 0.5 mm to 2 mm in width, and most specifically about 1 mm in width. The joining zones 28', 28" optionally can be impregnated with a hot melt or other barrier material to prevent wicking, or they can be embossed, perforated, partially slit, thermally fused, and the like.

Dotted lines 76', 76" show the unfolded position of the wing-like extensions 76 of the backsheet 14 prior to being folded into the longitudinal slit components 32, 34 of the unitary absorbent layer 18. In their folded-in state, the wing-like extensions 72 pass above the body-side surface of the outer portion 20 of the unitary absorbent layer 18 in the crotch region 42, then descend through the longitudinal slit components 32, 34 and pass beneath a portion of the garment-side surface of the central portion 22 to define optionally overlapping underlying portions 44', 44" of the wicking barrier 30. The overlapping underlying portions 44', 44" can be joined adhesively or by other means to increase the stability of the article and to hold the wicking barrier 30 in place.

Additional contouring or shaping of the central portion 22 can be achieved by insertion therebeneath of any of the following, none of which are shown: a central rising member (not shown), such as an absorbent central rising member, a thermoplastic deformation element, or a hinged resilient deformation element; an inflatable member; a gas filled bubble or pouch; a pouch or pocket filled with free flowing materials such as eucalyptus nits, hollow spheres of absorbent polymers or beads; a pledget of an absorbent material such as fluff pulp, an absorbent foam, or regenerated cellulose; and the like. The additional material may be above or below the underlying portions 44', 44" of the wicking barrier 30.

Figure 8A:
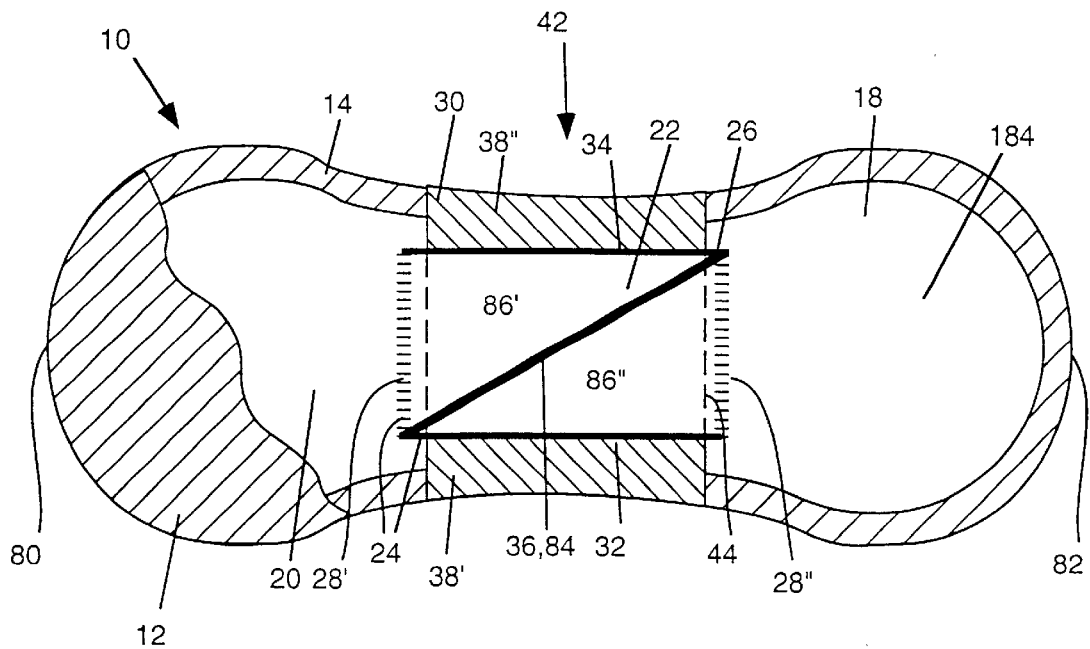
FIG. 8 depicts two embodiments with slits dividing the central portion of the unitary absorbent layer into two liftable regions.

FIG. 8A shows an embodiment of an article 10 having a front end 80 and a rear end 82, comprising a central portion 22 separated from the outer portion 20 of the unitary absorbent layer 18 by a boundary 24 comprising two joining zones 28', 28" and two longitudinal slit components 32, 34 of a continuous slit 26. The continuous slit 26 has a shape substantially resembling the letter "Z", meaning that two spaced apart substantially longitudinal slit components 32, 34 are joined by a substantially diagonal slit 84 (which also serves as a transverse slit component 36 by virtue of spanning the transverse distance between the longitudinal slit components 32, 34) joining a front end of one longitudinal slit component 32 to the back end of another longitudinal slit component 34 to form a continuous slit 26. The slit 26 divides the central portion 22 into two hinged sections 86', 86" which, prior to complete assembly of the article 10, can be lifted away from the plane of the unitary absorbent layer 18, remaining contiguously connected thereto by joining zones (hinge zones) 28', 28", which can be impregnated with hydrophobic material (not shown) if desired. The article 10 further comprises a polymeric film or web serving as a wicking barrier 30 in the crotch region 42. The wicking barrier 30 comprises horizontal components 38', 38" on or above the body-side surface of the unitary absorbent layer 18 and further comprises an underlying portion 44 beneath the central portion 22 of the unitary absorbent layer 18.

Figure 8B:
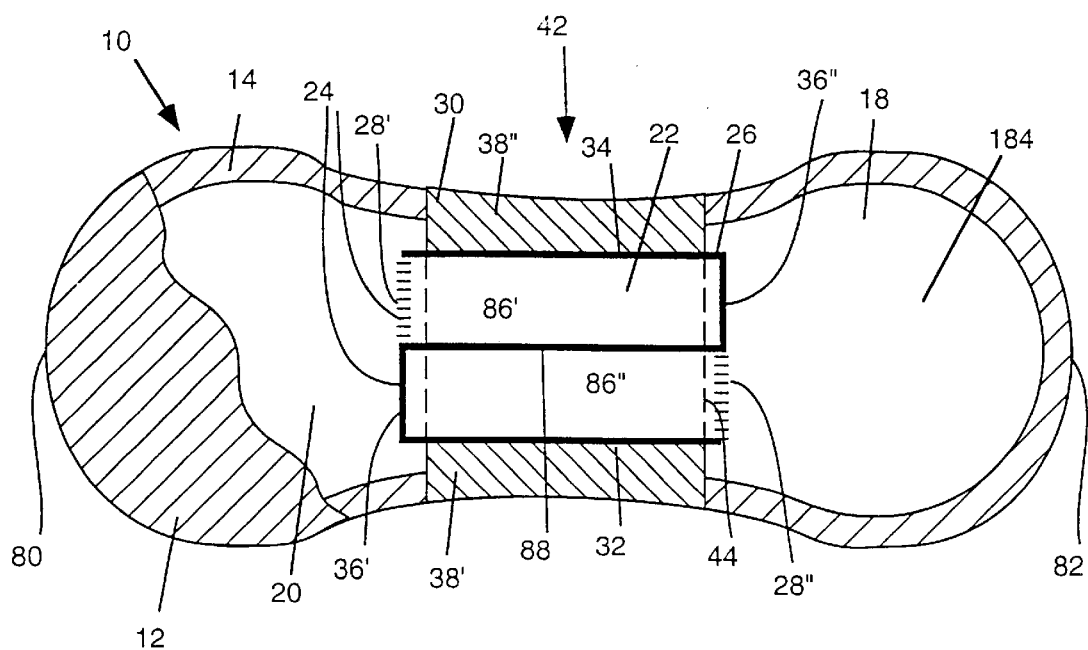

FIG. 8B depicts the article 10 of FIG. 8A with a modified slit 26. The modified slit 26 has a rectilinear "S" shape with two spaced apart substantially longitudinal slit components 32, 34 toward the longitudinal sides of the unitary absorbent layer 18, two substantially transverse slit components 36', 36" extending about halfway from one end of each of the longitudinal slit components 32, 34 toward the nearest end of the respective opposing longitudinal slit components, 32 or 34, joined substantially along the longitudinal centerline by a central longitudinal slit 88, which can also serve as a shaping line for promotion of upward deflection of the central portion 22. The slit 26 is continuous and establishes two hinge zones (joining zones) 28', 28" which are about 50% shorter than those of FIG. 8A.

The two hinged sections 86', 86" in both FIG. 8A and FIG. 8B can permit insertion of the wicking barrier 30 into the slit 26 after the unitary absorbent layer 18 is disposed on or attached to the backsheet 14, or prior thereto. The two hinged sections 86', 86" can both be lifted away from the plane of the unitary absorbent layer 18 at the respective hinge zones 28', 28" to permit insertion of strip of barrier material to serve as the wicking barrier 30, after which the hinged sections 86', 86" can be lowered back into place and optionally adhesively attached to the underlying portion 44 of the wicking barrier 30.

Figure 9:
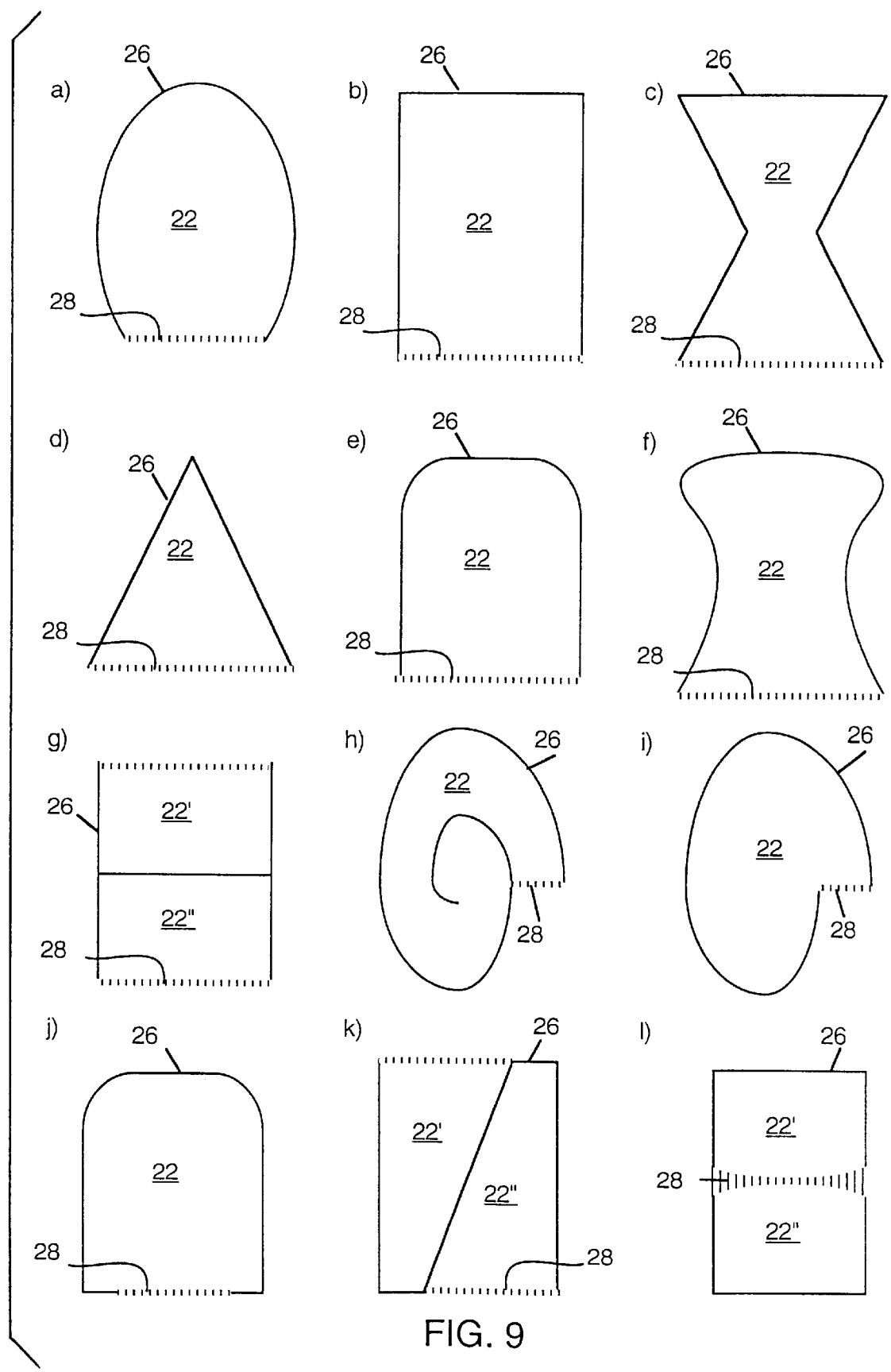
FIG. 9 depicts a variety of exemplary shapes for boundaries around the central portion of the unitary absorbent layer.

FIGS. 9A to 9L depict other shapes of boundaries comprising slits 26 and joining zones 28 that can surround the central portion 22 of a unitary absorbent layer (not shown). The slits 26 combined with the joining zones 28 in FIGS. 9A to 9L define boundaries that may be described as an ellipse truncated at one end (FIG. 9A), a rectangle (FIG. 9B), an angular hourglass (FIG. 9C), a triangle (FIG. 9D), a half-rounded rectangle (FIG. 9E), a bread load (FIG. 9F), twin shutters (FIG. 9G), a spiral (FIG. 9H), the outer perimeter of a spiral (FIG. 9I), a half-rounded rectangle with a narrowed joining zone 28 (FIG. 9J), opposing trapezoids (FIG. 9K), and flaps from a central joining zone 28 (FIG. 9L). The slits 26 of FIGS. 9A to 9L have similar shapes, including an ellipse truncated at one end (FIG. 9A), three sides of a rectangle (FIG. 9B), the upper portion of an angular hourglass (FIG. 9C), a "V" shape (FIG. 9D), the upper portion of a half-rounded rectangle (FIG. 9E), the upper portion of a bread load (FIG. 9F), an "H" shape (FIG. 9G), a spiral (FIG. 9H), the outer perimeter of a spiral (FIG. 9I), a horseshoe shape (FIG. 9J), an angular "S" shape (FIG. 9K), and a rectangle minus center hinges (FIG. 9L).

Depending on the geometry of the slits 26 in FIGS. 9A to 9L, there may be a single joining zone 28 or, as shown in FIG. 9K and in FIG. 8, two or more joining zones 28. In FIG. 9L, the joining zone 28 is flared at the ends and serves as a central hinge permitting folding about a central transverse axis of two sections of the central portion 22', 22". Thus, a joining zone 28 can form a relatively small fraction of the perimeter of a boundary that is otherwise occupied by one or more slits (two slits 26 forming a part of the boundary in FIG. 9L). Specifically, the joining zone 28 can occupy a portion of the boundary of about 70% or less, or about 50% or less, more specifically about 25% or less, more specifically still from about 5% to about 30%, and most specifically from about 5% to about 20%.

Figure 10:
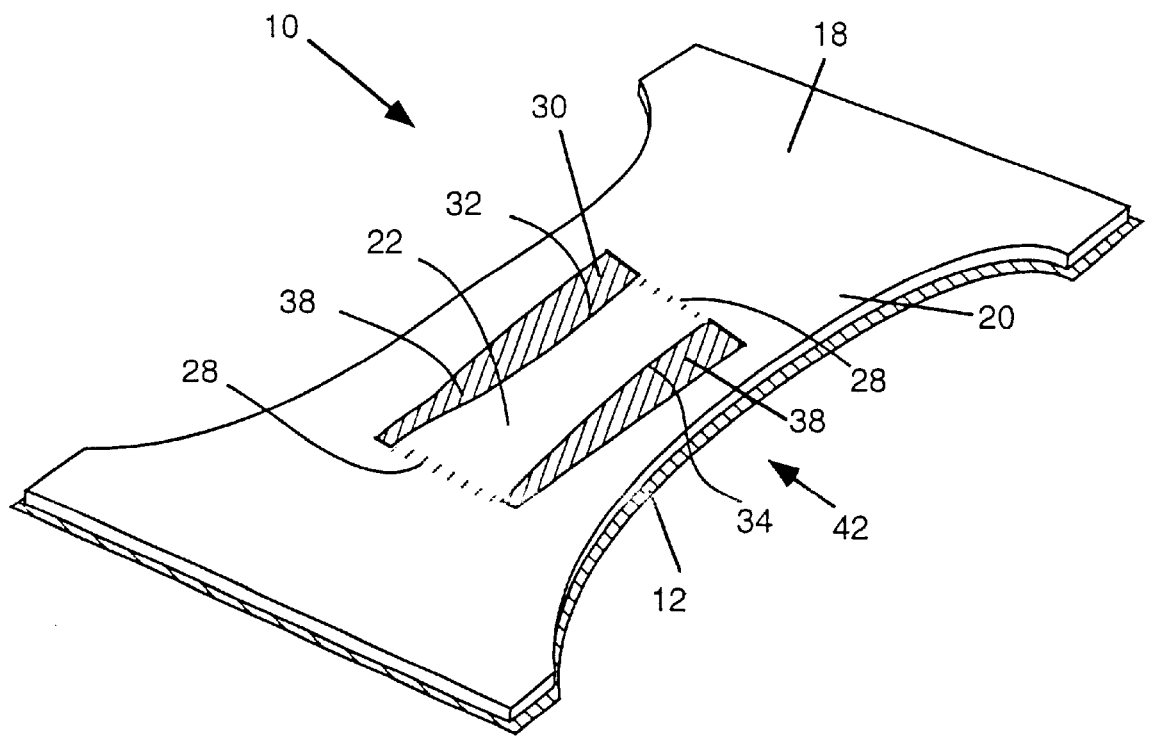
FIG. 10 depicts a diaper according to the present invention.

FIG. 10 depicts an absorbent article 10 that is a diaper according to the present invention. The article 10 comprises a unitary absorbent layer 18 superposed on a backsheet 12, and a topsheet (not shown for clarity). The outer portion 20 is separated from a central portion 22 by a pair of substantially longitudinal slit components 32, 34 and joining zones 28 between the ends of the longitudinal slit components 32, 34. A wicking barrier 30 comprises horizontal components 38 on the body-side surface of the unitary absorbent layer 18 covering a portion of the outer portion 20 in the crotch region 42. The wicking barrier 30 descends into the longitudinal slit components 32, 34 and passes beneath a portion of the central portion 22.

Additional components (not shown) can be added, including an underlying lower layer of densified airlaid material or wet laid material, either being optionally combined with superabsorbent material, to retain fluid by virtue of its higher capillary suction away from the body of the wearer. A surge layer can also desirably be added over the unitary absorbent layer 18, including a surge layer that is substantially coextensive with the central portion 22.

The central portion 22 need not extend into the back portions of the diaper where collection of feces rather than urine may be the objective. The region most likely to receive feces, particularly runny bowel movement, can be provided with additional voids and gaps in the unitary absorbent layer 18 to provide space for receiving bowel movement and holding it away from the skin of the user.

Figure 11:
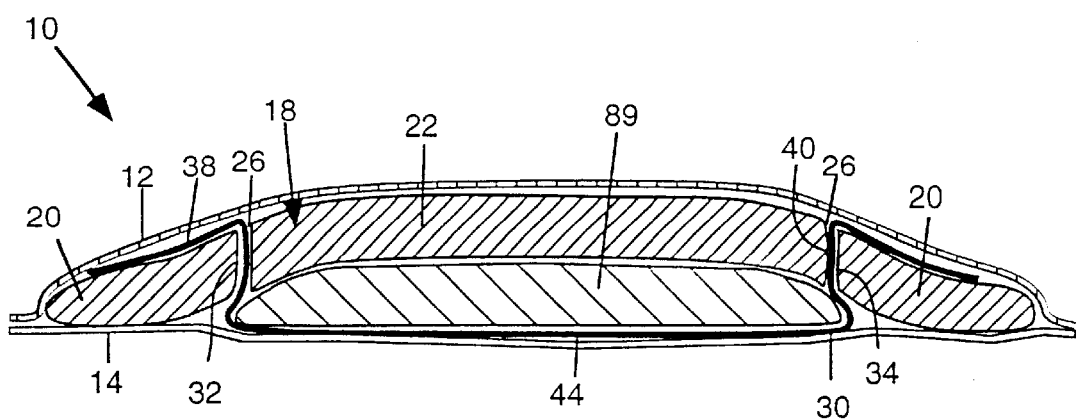
FIG. 11 depicts a method of slitting a unitary absorbent layer as the wicking barrier is brought through the unitary absorbent layer.

FIG. 11 depicts a transverse cross-section of an absorbent article 10 according to the present invention wherein the wicking barrier 30 has extended horizontal components 38 on the surface of the unitary absorbent layer 18, and wherein the unitary absorbent layer 18 is concave down due to the shaping effect of a narrower, underlying absorbent pledget 89 disposed below the central portion 22 of the unitary absorbent layer 18. The shaping effect caused by the narrow absorbent pledget 89 can help improve body fit during use. The combination of the absorbent pledget with the wider overlying unitary absorbent layer 18 serves as a deflection control element.

Figure 12:
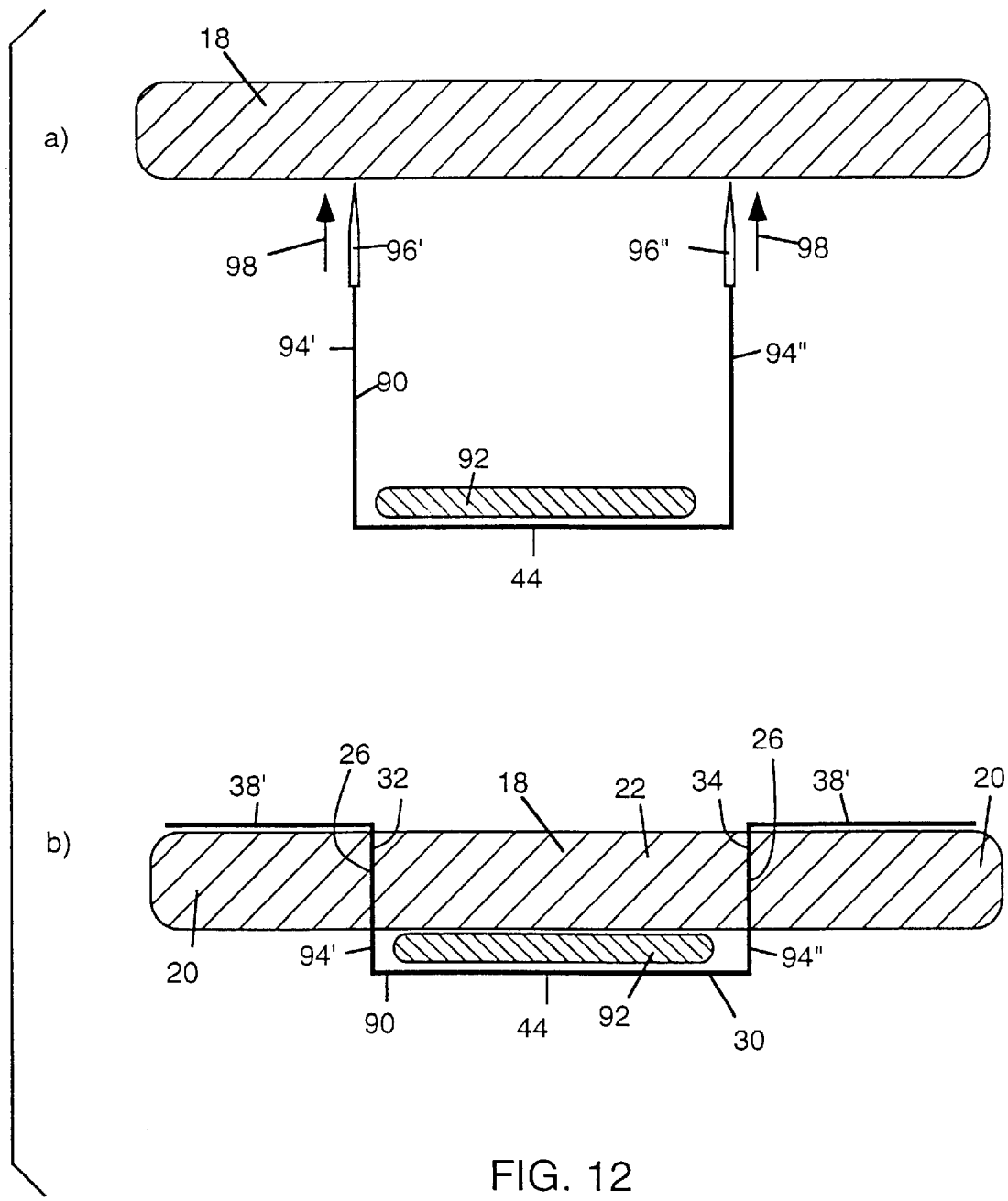
FIG. 12 depicts a cross-section of an absorbent article comprising a unitary absorbent layer above a narrower pledget, wherein the pledget causes the unitary absorbent layer to be concave down such that it is predisposed to deflect vertically upward during lateral compression.

FIGS. 12A and 12B depict one aspect of a method of making unitary absorbent layers according to the present invention. A first step in this method, shown in FIG. 12A, involves providing a previously formed, unslitted unitary absorbent layer 18 and a length of wicking barrier material 90 with an optional insert 92 (e.g., pledget or central rising member) disposed on a central underlying section 44 of the length of wicking barrier material 90. Side portions 94', 94" of the wicking barrier material 90 are attached to penetration means, shown here as knife blades 96', 96". The attachment can be by clamping, adhesion, frictional engagement (e.g., being looped through slots in the knife blades 96', 96"), and the like. The knife blades 96', 96" are then driven through the unitary absorbent layer 18 in the direction shown by arrows 98. For example, the knife blades 96', 96" can be pushed, propelled, shot, and the like such that the blades penetrate the unitary absorbent layer 18 and pull the wicking barrier material 90 through the slits 26 that are created by the piercing action of the blades 96', 96". Once the blades 96', 96" have penetrated the absorbent layer 18, the wicking barrier 30 is separated from the blades blades 96', 96" (e.g., unclamped, it can be cut from the blades, unadhered, and the like) and the portions of the wicking barrier 30 extending above the body-side surface of the unitary absorbent layer 18 are lowered to be against the unitary absorbent layer 18 and directed laterally outwards, as shown in FIG. 12B, to form horizontal components 38', 38" on or above the body-side surface of the unitary absorbent layer 18 having a pair of opposing longitudinal slit components 32, 34 forming part of the boundary between a central portion 22 and an outer portion 20, with a wicking barrier 30 spanning the thickness of the unitary absorbent layer 18 throughout a major portion of the length of the opposing longitudinal slit components 32, 34.

Figure 13:
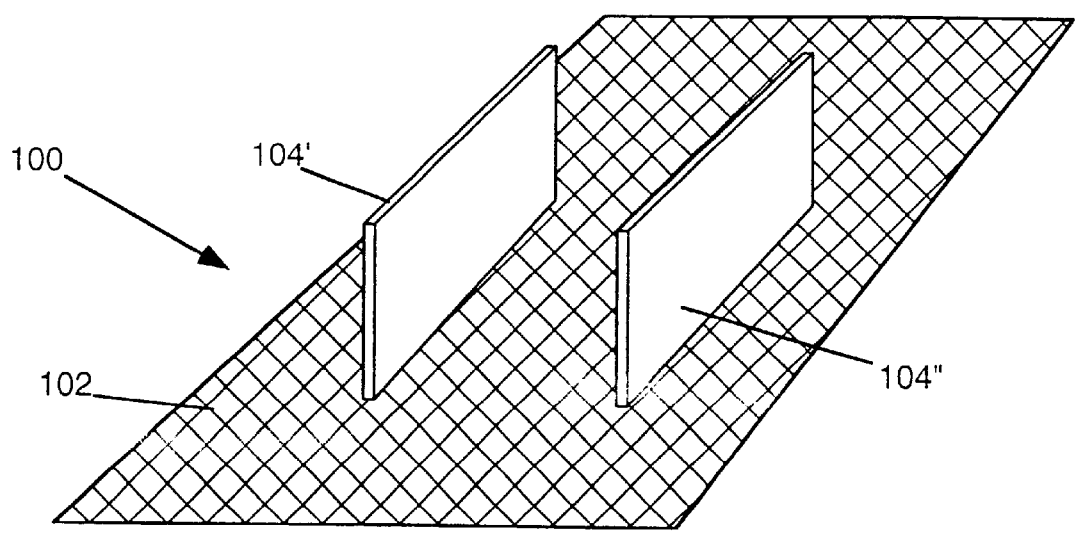
FIG. 13 depicts an air laying surface for forming integral slits in an air laid web through which a wicking barrier can be pulled.

FIG. 13 depicts an air laying device 100 useful in producing articles of the present invention by air laying. The air laying device 100 comprises a metallic porous mesh 102 through which air can pass but on which fibers entrained in air are retained to form a mat. Two thin fins 104', 104" project vertically from the surface of the device 100. During air laying, the fins 104', 104" will naturally provide slits in the air laid material and can subsequently be attached to a web of barrier material to pull the barrier material through the slits as the air laid web is removed from the porous surface of the porous mesh 102.

FIG. 14A shows a cross section of an air laid web 106 after it has been formed on the device 100 in FIG. 13, with the cross section passing through the fins 104', 104" of FIG. 13. The web resides on the porous mesh 102. Next, as shown in FIG. 14B, the portions of the fins 104', 104" projecting above the upper surface of the web 106 are attached to a length of a film or other wicking barrier material 90 that traverses the exposed portions of the fins 104', 104" and spans the two fins 104', 104". The web 106 is then removed from the porous mesh 102 and carried vertically upward, in the direction shown by the arrow 98. The wicking barrier material 90 may be attached to the fins 104', 104" adhesively, by clamping, by frictional engagement, or by other means, provided that the wicking barrier material 90 and the fins 104', 104" can be pulled through the web 106 to pull the wicking barrier material 90 into the slits 26 in the web 106 to define a wicking barrier 30 in the unitary absorbent layer 18. After the web 106 is pulled away from the fins 104', 104", the wicking barrier material 90 is spread laterally outwards to form the configuration of the wicking barrier 30 shown in FIG. 14C, wherein the wicking barrier 30 passes through the slits 26', 26" and extends on a surface of the web 106 to form horizontal components 38', 38" on the lower surface. As shown, the lower surface of the web 106 is intended to be the body-side surface of the unitary absorbent layer 18 made from the web 106.

A central rising member, central inflatable member, absorbent pledget, pouch of free flowing particles, resilient deformation element, or other members, none of which are shown, could be disposed over the absorbent web 106 before the wicking barrier material 90 is pulled through the slits 26', 26" formed during the air laying process. In this manner, the added components would be held between the wicking barrier 30 and the garment-side surface of the unitary absorbent layer 18.

Figure 15:
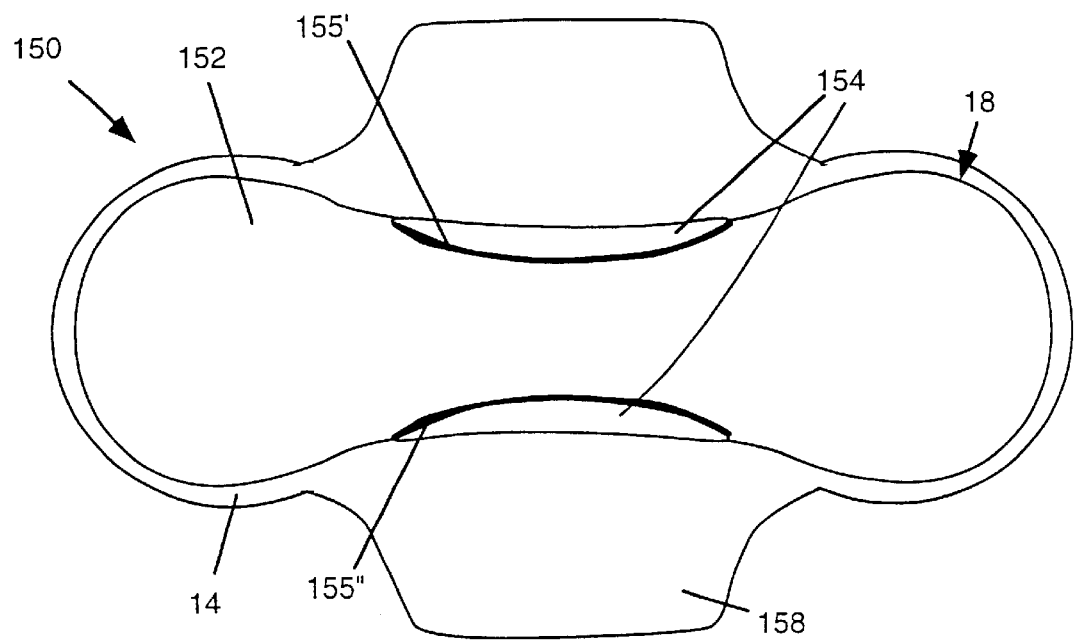
FIG. 15 depicts a commercial maxipad.
Figure 16:
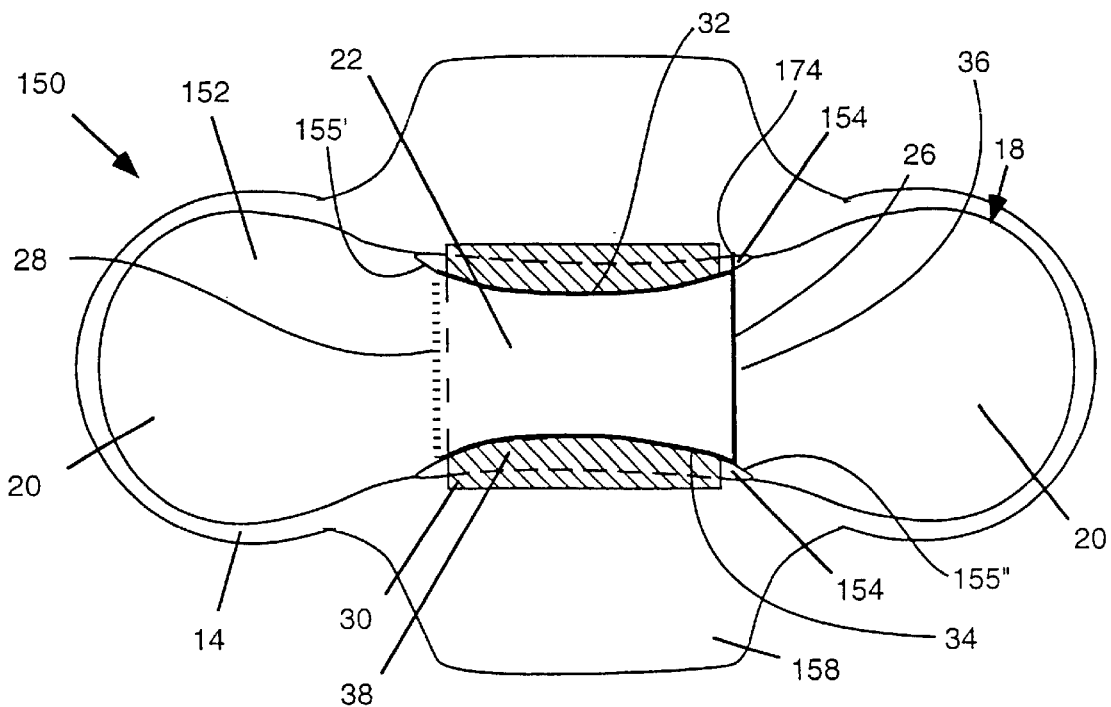
FIG. 16 depicts modifications of the commercial maxipad of FIG. 15 corresponding to the present invention.

FIGS. 15 and 16 are discussed in the Examples below.

Without limitation, further principles for construction of absorbent articles according to the present invention are given below in terms of the specific components.

The Central Rising Member

By way of example, the central rising member whether fibrous or not can have a basis weight of from about 30 grams per square meter (gsm) to about 800 gsm, more specifically from about 50 gsm to about 500 gsm, more specifically still from about 50 gsm to about 300 gsm, and most specifically from about 70 gsm to about 270 gsm.

Desirably, the central rising member comprises at least one ply of a resilient material having a wall thickness wherein the resilient material defines an internal void space due to folding or layering of the material, wherein the z-direction thickness of the internal void increases in size during lateral compression as the upper surface of the central rising member is displaced upward. Alternatively, the central rising member can lack an internal void, being a single layer of material that is folded or creased to form an inverted V-shape or U-shape when the longitudinal sides thereof are moved inward toward the initial longitudinal centerline of the central rising member.

The central rising member can comprise a thermoplastic deformation element as disclosed by K. B. Buell in U.S. Pat. No. 5,300,055, issued Apr. 5, 1994, but the central rising member can also be non-thermoplastic such as a densified cellulosic web. Thus, the central rising member can have a flexure means, and particularly a longitudinally extending flexure hinge, for inducing the body facing surface of the central rising member to have a convex upward configuration when the sanitary napkin is worn. In an alternative embodiment, the deformation element has a central region having a "W" shaped cross-section wherein the body facing surface of the central rising member having the convex upward configuration is located in the central region, generally symmetrically between the longitudinal side edges of the napkin. In another embodiment, the central rising member has a cup-shaped front region and a back region having a convex upward configured body-facing surface.

Preferably, the central rising member should be resilient enough that it can lift a load of 50 grams by at least 4 mm when it is resting on a solid surface and the longitudinal sides are laterally compressed toward the longitudinal centerline of the central rising member such that the longitudinal sides thereof are brought no more than 13 mm closer due to lateral compression. Rectangular blocks 50-mm long and 5-mm square in cross section, with the 50-mm long dimension aligned with the longitudinal sides of the central rising member, can be used to evenly displace the longitudinal sides toward one another. The load to be lifted is a vertically oriented spindle and foot on a device such as a Mitutoya Digimatic Indicator (e.g., Model 543-525-1). The foot is a stiff section of acrylic plastic 0.7 mm in thickness, 50 mm long and 20 mm wide, placed over the central rising member and centered beneath the spindle of the indicator to more evenly distribute the load of the spindle. The vertical displacement caused by the lateral compression of the longitudinal sides of the central rising member is the vertical distance traveled by the spindle.

The central rising member desirably can still perform its function even when fully wetted. Thus, the central rising member desirably has a degree of wet resiliency, and specifically has a Springback of about 0.7 or greater, as defined in U.S. Pat. No. 5,672,248, issued to Wendt et al. on Sep. 30, 1997. In one related embodiment, the elastic modulus (based on machine direction tensile testing with a crosshead speed of 10 in/min, jaws 2 inches wide, and a gauge length of 2 inches) of the central rising member does not decrease by more than about 30% after being uniformly wetted for five minutes with an amount of distilled water equal to the dry mass of the central rising member, and more specifically does not decrease by more than about 20%. In another embodiment, the elastic properties of the central rising member are substantially unaffected by moisture.

In another embodiment, the central rising member can be a web or layer of resilient material, including a cellulosic densified airlaid web, which is predisposed to deflect vertically upward by virtue of a central hinge element, a shaping line, or a score mark created by creasing or folding the central rising member along its longitudinal centerline. On the garment-side surface of the central rising member, disposed on opposing sides of the longitudinal centerline (or on opposing sides of a central scoremark or shaping line), are attachment means which join together upon contact and hold the opposing sides of the central rising member together to maintain an upwardly flexed shape (e.g., a mountain fold configuration) even when the inward compressive forces that brought the opposing attachment means together are subsequently removed. Velcro® and other known mechanical attachment means can be used. The attachment means can also be magnetic wafers of buttons; adhesive materials; interlocking plastic ridges such as those used to seal resealable plastic bags, including ZIPLOC® bags; plastic or metallic snaps; and the like.

In the absorbent article of the above embodiment, the central rising member can further comprise a garment-side surface, and the attachment means can comprise a first attachment section on the garment-side surface of the first portion of the central rising member and a second attachment section on the garment-side surface of the second portion of the central rising member, wherein the first attachment section connects to the second attachment section when the garment-side surface of the first portion of the central rising member is brought into contacting relationship with the garment-side surface of the second portion of the central rising member. The attachment means can comprise a mechanical attachment means such as a hook and loop system disposed on the garment-side surface of the central rising member.

In other embodiments, the central rising member can also comprise a liquid pervious spacing structure for moving the topsheet away from the core, as disclosed by R. B. Visscher et al. in U.S. Pat. No. 5,324,278, issued Jun. 28, 1994.

The central rising member can have a flexure resistance of about 50 grams or more, more specifically about 100 grams or more, and more specifically still about 300 grams or more. Increased flexure resistance generally correlates with increased shaping ability of the central rising member, but high flexure resistance can also mean increased stiffness of the article and increased discomfort. Desirably, the flexure resistance of the central rising member is less than 1000 grams and more specifically less than 500 grams. In some cases, good performance can still be achieved when the central rising member has a relatively low flexure resistance, such as a resistance less than 100 grams, more specifically 90 grams or less, and most specifically about 80 grams or less, particularly when the central absorbent member itself is provided with bending lines and more particularly when adhesive bonds join the central absorbent member to at least one portion of the central rising member, such that the central rising member can promote upward deflection without significant stiffness and with very little risk of discomfort to the wearer.

In some embodiments, the central rising member can be wider than the central void of the outer absorbent member. For example, an absorbent article can comprise an outer absorbent member with a central elliptical hole therein. An absorbent central rising member can be disposed beneath the outer absorbent member such that a portion of the absorbent central rising member is in the hole, but side portions such as tapered sides of the central rising member can extend beyond the walls of the void and be disposed beneath the outer absorbent member.

The Central Inflatable Member

In contrast to a central rising member, which generally relies on lateral compression to cause the upward deflection for improved body fit, a useful alternative is a central inflatable member which can deflect a central portion of the unitary absorbent layer upward toward the body without necessarily requiring lateral compression to cause upward deflection. Thus, an inflatable bladder or envelope may be provided below the central portion, wherein the bladder can be filled with a gas to become inflated and thus urge the central portion of the unitary absorbent layer upward. The gas may be provided by a small deformable pouch with a one-way air intake valve that can be pumped by body motion or by action of the fingers to drive air into the bladder, which also has a one-way valve or flap to hold air in the bladder but to permit its entry. The central inflatable member may also be or comprise a sealed expandable component as disclosed in U.S. Pat. No. 5,520,674, "Disposable Absorbent Article Having a Sealed Expandable Component," issued May, 28, 1996 to Lavon et al. The sealed expandable component comprises a compressed, resilient element disposed within an air impermeable envelope. The compressed element provides the absorbent article with a thin, low bulk profile prior to use of the disposable absorbent article. At the point of use of the absorbent article, the air impervious envelope is opened, thereby permitting entry of air into the envelope and expansion of the compressed element. Alternatively, the air impervious envelope may be opened by the compressive action of the user's legs to allow inflation of the sealed expandable component only after the article is in place against the body of the wearer. The sealed expandable component may be sealed by a small section of tape or film which ruptures or is dislodged when the article is compressed. The sealed expandable component is opened by compressive action of the user, the central inflatable member can be classified as a central rising member as well. Further, when the central inflatable member is further provided with upward deflection by laterally inward compression, the central inflatable member can also be classed as a central rising member.

In a preferred embodiment, the expandable component comprises a compressed resilient element disposed within an air impermeable envelope. The air impermeable envelope can be evacuated, such as by vacuum sealing, to have an internal pressure less than the outside atmospheric pressure. The expandable component expands from a first thickness to a second thickness greater than the first thickness upon opening of the air impermeable envelope.

The air impermeable envelope can comprise a port having a releasable closure. The releasable closure can be removed at the point of use of the disposable absorbent article to permit air to enter the envelope through the port, thereby providing expansion of the expandable component. In one embodiment, the releasable closure can be resealable, so that air drawn into the port does not escape when the expandable component is subjected to compressive loading.

The resilient element can be porous, so that when the releasable closure is removed from the port, expansion of the resilient element draws air into the resilient element, as well as into the space in the envelope not occupied by the resilient element. In one such embodiment, the resilient element can comprise an open celled polymeric foam.

The resilient compressed element is preferably porous, so that when a releasable closure is removed from a port in the air impermeable envelope, expansion of the resilient element draws air into the resilient element, as well as into the space in the cavity within the air impermeable envelope not occupied by the resilient element. In one such embodiment, the resilient element can comprise a porous sponge. In another embodiment, the resilient element can comprise an open celled foam, such as an open celled polymeric foam. By open celled it is meant that the individual cells of the foam are for the most part not completely isolated from each other by the polymeric material of the cell walls. Open celled foams, as used herein, can include foams which are initially closed celled, and which are reticulated, such as by compression, to form an open celled structure within tile envelope.

One suitable porous foam from which the resilient element can be made is polyurethane foam, such as is available as #1230 foam from the American Excelsior Corp. of Cincinnati, Ohio. Another suitable porous, open celled foam is a foam prepared by polymerizing a high internal phase emulsion, such as is described in U.S. Pat. No. 5,147,345; High Efficiency Absorbent Articles for Incontinence Management, issued Sep. 15, 1992 in the name of Young et al.

The central inflatable member can comprise an initially collapsed bladder with a one-way intake valve that can be manually expanded prior to or during use. Alternatively, a simple sealing mechanism such as an adhesive tab over an intake port may be used to permit the user to manually allow air in or out of the bladder to adjust the degree of inflation. Inflation may be provided by internal expandable components, such as compressed resilient sponge materials, or by the user pulling out one surface of the bladder to create internal void volume that can pull air into the bladder.

The bladder or air impermeable envelope can be formed from two adjacent layers of polymeric film joined along the periphery of a boundary such as a circle or oval, wherein the central portion of the two joined films are not joined to one another but can be separated from one another to provide a void space therebetween. Thus, a wicking barrier and a backsheet can function together as a bladder or air impermeable envelope, with thermal, ultrasonic, or adhesive bonding around a periphery, and a resealable closure or one-way valve means over a port on the backsheet can be opened to permit the user to stretch the backsheet away from the wicking barrier to create a void space therebetween which is filled with air as it flows through the temporarily opened port. Once the void space is filled with air, the port is then sealed or a one-way valve means prevents exit of the air, such that the bladder or envelope becomes filled and can urge the central portion of the unitary absorbent layer thereabove toward the body of the user, particularly when the article is worn and compressed by the legs of the user.

Space between two gas impermeable film layers or, more generally, within a bladder or gas impermeable envelope can also be filled with internal gas production means within the bladder or envelope. Reagents such as vinegar and baking soda can be reacted to release carbon dioxide, when a barrier or seal separating the two reagents is broken or removed. Many other known gas producing agents can be used, including those that are encapsulated and yield gas only when the capsules are broken. Non-toxic blowing agents known in the art of foam production may also be used. Several related embodiments are disclosed in U.S. Pat. Nos. 3,881,491 and 3,921,232 issued to Whyte on May 6, 1975 and Nov. 25, 1975, respectively. The Whyte patents disclose disposable absorbent articles having self-inflating structures. The self-inflating structures include a wall of semipermeable material and a gas evolving material. Upon exposing the outside of the semipermeable wall of the structure to an activator material such as urine or other body fluids, the activator material permeates the structure to interact with the gas evolving material, whereby the structure becomes inflated by evolved gas. Similarly, U.S. Pat. No. 5,876,393, issued to N. A. Ahr et al. Mar. 2, 1999 teaches the use of an inflatable or expandable component that includes a gas evolving material and an activating material separated from the gas evolving material by a breakable barrier. The barrier is broken to combine the materials and inflate the component at the point of use of the disposable absorbent article.

The means for expanding the component include a first material, a second material and a breakable barrier separating the first and second materials. The first and second materials can be combined at the point of use of the absorbent article by breaking the barrier. One of the first and second materials can swell or evolve a gas upon combining the first and second materials. The component is thereby expanded from a first thickness to have a predetermined shape having a second thickness substantially greater than the first thickness. In a preferred embodiment the expandable component is inflatable and includes one or more inflatable chambers. The inflatable component includes a gas evolving material and a liquid impervious breakable packet containing a liquid activating material. The gas evolving material and the packet can be disposed in a gas permeable, hydrophobic envelope. The packet is breakable by the user at the point of use of the absorbent article to combine the activating material with the gas evolving material. The gas evolved by the combination of the two materials inflates one or more inflatable chambers. In one embodiment the expandable component comprises an inflatable spacer disposed between the topsheet and backsheet.

The first and second materials and should be non-toxic and combine to evolve an inert gas which is non-toxic in the quantities generated. The first gas evolving material is preferably a combination of a bicarbonate, such as sodium bicarbonate or potassium bicarbonate, with a powdered acid to provide carbon dioxide when wetted by the second activating material. Suitable powdered acids include, but are not limited to citric acid, tartaric acid, terephthalic acid, and salicylic acid. A suitable first material comprises an effervescent powder containing heat treated sodium bicarbonate, citric acid, and salicylic acid and is available in tablet form from Miles, Inc. of Elkhart, Ind. under the trade name ALKA-SELTZER.

The first material is preferably soluble in the second activating material. The preferred second activating material comprises water. In an alternative embodiment, the first material can comprise a bicarbonate and the second activating material can comprise one of the above listed powdered acids dissolved in water.

Methods of Making

Generally, automated equipment can be used similar to the production lines already used for production of sanitary napkins, diapers, and the like, with minor modifications to produce the present invention. Modular systems are especially preferred, wherein the various unit operations in the production line can be moved and replaced with other modules without necessitating a complete rebuild of a machine.

The production line can include a hammermill for production of comminuted fibers, if fluff pulp is to be used, or absorbent material in roll form can be provided, including airlaid webs, coform, mechanically softened pulp sheets, tissue webs, and the like. Likewise, the nonwoven or film components of the absorbent article are also generally provided in roll form. Roll goods are unwound and cut to shape, using methods such as die cutting, slitters, or water jets, and the components placed in proper relationship one to another, typically with online bonding at selected regions provided by spray adhesive, contact with ultrasonic horns or heated embossing elements, or other bonding means known in the art. Components may be moved on continuous belts from one operation to another, and may be further transported with vacuum pick up shoes, jets of air, mechanical pincers, and the like.

For example, a web of nonwoven material or coform of width suitable for the absorbent core of an absorbent article may be unwound and provided with pairs of longitudinal slits spaced apart in the machine direction such that one opposing pair of longitudinal slits shorter than the length of the unitary absorbent layer exists in each unitary absorbent layer after the articles are cut and assembled. A length of wicking barrier material such as a poly film can then be threaded into the absorbent core such that the strip is brought over the unitary absorbent layer from a first longitudinal side, threaded into a first slit, drawn under the unitary absorbent layer across the space between the two opposing slits, and then threaded through the second slit and further drawn transversely across the remainder of the absorbent core toward the second longitudinal side.

A central portion of the unitary absorbent layer is defined by the longitudinal sides slits. Under the central portion, a central rising member can be disposed or attached, including an "e"-folded resilient, thin, absorbent fibrous web adhesively attached to the wicking barrier.

A backsheet is then attached to the garment-side surface of the unitary absorbent layer and a topsheet is disposed over the body-side surface thereof and attached to the backsheet.

The embodiment of FIG. 2 can be readily manufactured in several ways. In one method, such as that already discussed in connection with FIG. 12, a strip of barrier material is prepared with an optional pledget or central rising member disposed centrally on the strip. The strip is centered beneath a unitary absorbent layer and longitudinal sides of the strip are pulled upward into the unitary absorbent layer, either through previously made slits or through slits that are created as the longitudinal sides of the strip are moved upward, as can be achieved by attaching the strip to two blade elements which pass through the unitary absorbent layer, carrying the sides of the barrier strip therethrough. The sides of the barrier material are pulled up through the unitary absorbent layer until the optional centrally disposed central rising member or pledget is held against the core. The sides of the barrier strip are then placed flush against the body-side surface of the unitary absorbent layer (or, more generally, against the body-side surface of the absorbent core), directed toward the longitudinal sides thereof. Alternatively, slits in the unitary absorbent layer can first be provided, and the central portion of the unitary absorbent layer between the slits can be elevated or deflected upwards to provide a passage beneath the central portion through which a strip of film or other barrier material can be pulled sideways (laterally) through the slits and under the central portion of the unitary absorbent layer, with the sides of the strip covering the body-side surface of the absorbent core in the crotch region (or target region) between the slits and the nearby longitudinal sides of the article.

Figure 14:
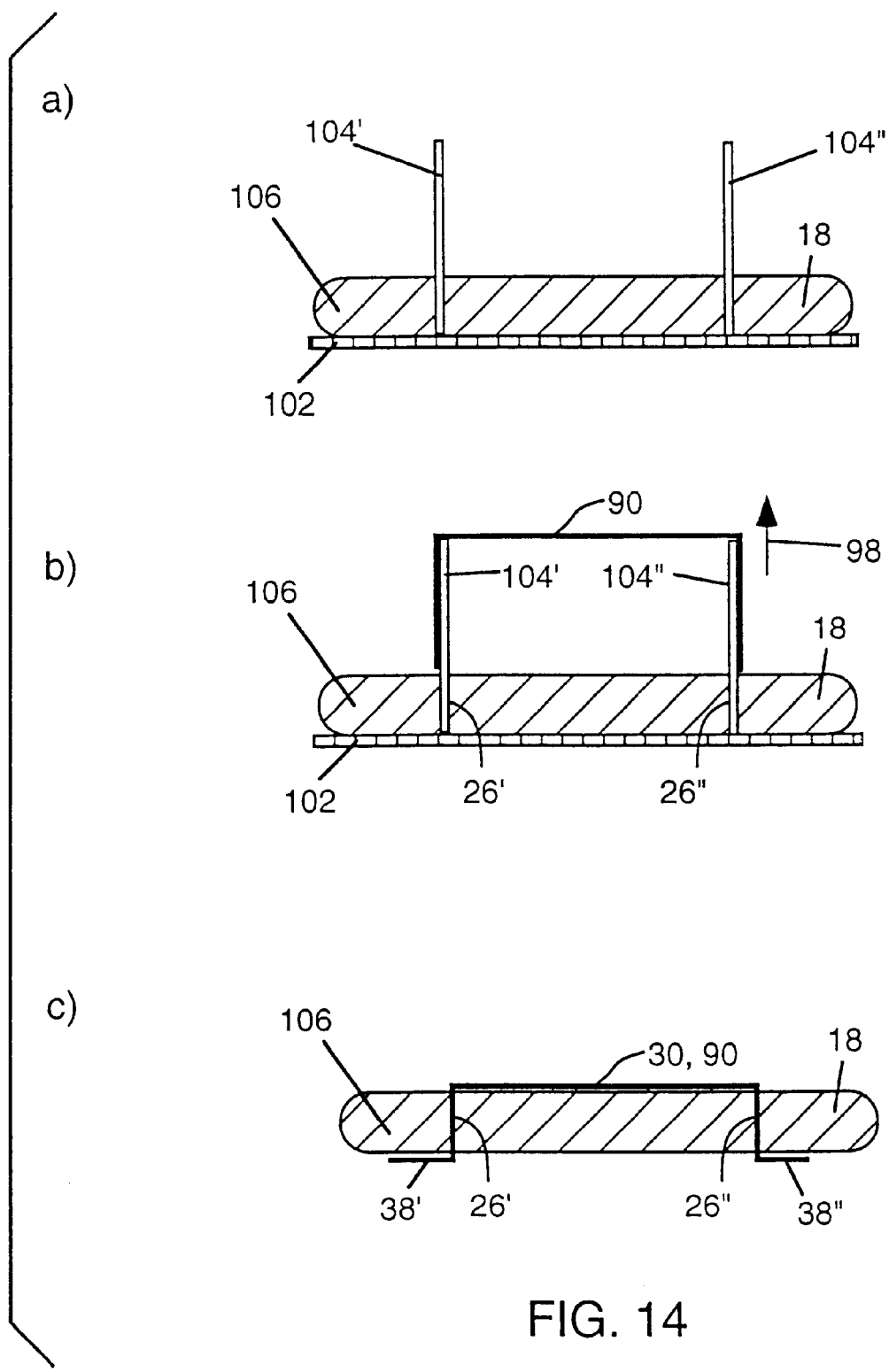
FIG. 14 depicts a portion of the method of pulling a wicking barrier through integrally formed slits in an air laid web made on the surface of FIG. 13.

Slits can be formed in the unitary absorbent layer during airlaying or other processes, such as by forming a web on an airlaying surface having vertical fins projecting above it, as was previously discussed in connection with FIG. 14. The fins can then be attached to wicking barrier material and pulled through the airlaid web to provide wicking barrier material in a portion of the boundary between a central portion of the unitary absorbent layer and an outer portion. The topsheet and backsheet can then be added and attached one to another.

In another embodiment, a portion of an wicking barrier may be present during airlaying such that a slit is naturally formed around a section of wicking barrier material. The material can then be pulled further through the web and inserted through a second slit that is formed in a separate slitting event or formed by forcing an end of the wicking barrier material through the absorbent web.

EXAMPLES

Several examples of absorbent articles were made with the materials listed in Table 1 below:

TABLE 1

Basic materials used in construction of absorbent articles for the Examples.

| Component | Manufacturer | Description |
|---|---|---|
| Topsheet | | |
| Spunbond material | Kimberly-Clark Corp. | 0.6 osy polypropylene spunbond web, "Delta" version, treated with 0.3% add-on of surfactant (described below), pin apertured |
| Surfactant treatment | ICI Americas, Inc. | 45% (w) polyethoxlated hydrogenated ethoxylated castor oil; 55% (w) sorbitan monooleate |
| Adhesive | National Starch and Chemical Co. | NS-34-5610: slot-coated, pinstripe pattern, applied at a level of about 5 gsm or less. |
| Fluff | Kimberly-Clark Corp. | Coosa River CR54 debonded softwood pulp comminuted with a hammermill |
| Densified airlaid webs | | |
| Completed web | Concert Fabrication, Ltee | 90% softwood fibers and 10% binder fibers with overall densities of 0.1–0.2 g/cc. |
| Fibers | Weyerhaeuser Co. | NB-416: bleached southern softwood kraft |
| Binder fibers | Hoechst Celanese Corp. (Trevira Company) | Celbond #255: PET core, activated co-polyethylene sheath, 50/50 core/sheath ratio, concentric, 2.8 dpf, with T-255 fiber finish |
| Coform | Kimberly-Clark Corp. | 60% bleached kraft southern softwood, 40% polyethylene, basis weight of 135 gsm |
| Impervious wicking barrier | | |
| Polyolefin film, white | Edison Plastics Co. | A low density polyethylene, 18 gsm, opaque with added white pigment, about 1 mil |
| Pervious wicking barrier | | |
| Spunbond web | Kimberly-Clark Corp | 0.8 osy 2.7 denier, rose color, no surfactant |
| Backsheet | | |
| Polyolefin film | Edison Plastics Co. | Low density polyethylene, 20 gsm, rose colored |
| Adhesive | National Starch and Chemical Co. | NS-34-5610, less than 15 gsm added, slot-coated, pinstripe pattern |
| Garment adhesive | National Starch and Chemical Co. | NS-34-5602, less than 45 gsm applied, slot coated, two 15 mm side lines of adhesive with a 19 mm space between them |
| Release paper | Akrosil Inc. | White base sheet, one side coated with silicone release agent, other side printed |

Example 1

Example 1 was made generally according to article 40 of FIG. 2, but with a central pledget disposed beneath the central portion 22.

In Example 1, the unitary absorbent layer comprised coform having a basis weight of 135 gsm having a length of 22 cm and a width of 6.7 cm. In the crotch region, two parallel, longitudinal slits in the unitary absorbent layer were manually cut with a rotary knife, the slits having a length of 7 cm, longitudinally centered and equidistant from the longitudinal centerline, being inset 1.1 cm from the longitudinal sides of the unitary absorbent layer. In the crotch region, the slits defined a central portion of the unitary absorbent layer between the slits, and the 1.1 cm-wide side regions of the unitary absorbent layer in the crotch region were the crotch region portion of the outer portion of the unitary absorbent layer. Wicking barrier material with slot coated adhesive on one side (using the adhesive available for the backsheet material in Table 1 and provided with release paper) was cut to a width of about 11 cm and a length of 6 cm. With the release paper still attached, the strip of wicking barrier material was placed over a first crotch region portion of the outer portion of the unitary absorbent layer, inserted through a first slit and under the central portion of the unitary absorbent layer, and the brought back up through the second slot and onto the body-side surface of the second crotch region portion of the outer portion of the unitary absorbent layer, and transversely centered so an equal portion of wicking barrier material extended past the longitudinal sides of the unitary absorbent layer. The release paper was then gradually removed while holding the wicking barrier material in place. The wicking barrier material had the adhesive side away from the body side of the article. The wicking barrier material extending past the longitudinal sides of the article was wrapped around the edges of the crotch region portions of the outer portion of the unitary absorbent layer and allowed to make contact with the central portion of the wicking barrier material under the central portion of the unitary absorbent layer. The release paper was completely removed and the wicking barrier material was folded around the longitudinal sides of the article, such that the wicking barrier material formed a wicking barrier covering a majority of the crotch region portion of the outer portion of the unitary absorbent layer and wrapping the longitudinal sides of the unitary absorbent layer.

A pledget of fluff pulp, having a basis weight of 680 gsm and a density of 0.14 cc/g, was cut to a length of 5 cm and a width of 2.5 cm and put through a slit and placed under the central portion of the unitary absorbent layer and above the underlying wicking barrier material with the length direction of the pledget aligned with the longitudinal centerline of the article. The unitary absorbent layer with the wicking barrier and pledget were placed on a rose colored web of backsheet, the adhesive side up, and a nonwoven topsheet was placed over the unitary absorbent layer and pressed into contact with the backsheet around the edges of the unitary absorbent layer. It was then cut to shape, leaving a periphery around the unitary absorbent layer. The final pad was 238 mm long and 80 mm wide, with a dogbone shape.

When inwardly laterally compressed, the crotch region of the absorbent article exhibited good vertical deflection as compressive forces urged the central portion into a more strongly upwardly convex shape and the crotch region portions of the outer portion of the unitary absorbent layer were deformed upward. The front and back portions of the article cupped upward with upward deflection angles of about 20 degrees from horizontal caused by inward compression on the transverse centerline caused by fingers moving inward to have a width of about 4 cm between the sides of the unitary absorbent layer.

Instead of a pledget of fluff pulp, any known central rising member or central inflating member could be inserted under the central portion of the unitary absorbent layer, either above or below the wicking barrier. The central rising member beneath the central portion of the unitary absorbent layer could be a section of densified airlaid web with a basis weight of 175 gsm and a density of 0.1 g/cc, cut to dimensions of 110 mm by 70 mm and folded with two creases normal to the long direction and evenly spaced apart to yield an "e"-folded web with a width of about 40 mm and a length of 70 mm. The creases defining the folds would be oriented in the longitudinal direction of the article so that the e-fold shape of the central rising member would be evidence in a transverse cross-section.

The backsheet could be provided with adhesive strips and release paper for attachment to the garment. For example, garment-contacting adhesive could be provided in two 15-mm wide, 190-mm long longitudinal strips leaving the central region about the longitudinal centerline free of adhesive. The placement of adhesive bands can be optimized to promote better control of deformation of the pad in use to better establish a W-fold geometry.

Example 2

For Example 2, a commercial pad made by Procter and Gamble was modified according to the present invention. An ALWAYS® Ultra Thin Long Maxi pad with flexible wings was obtained from a promotional distribution to residences in Appleton, Wis. during February of 1999. The pad is provided with a DRI-WEAVE® apertured film cover and a "Gel-Core" absorbent layer apparently comprising superabsorbent particles. The absorbent core, upon examination of the pad, contains two seemingly air-laid layers, with the lower layer provided with superabsorbent particles. Both layers had a length of about 25 cm and a width of about 7 cm in the crotch region to about 8.5 cm near the front and back portions. The packaging indicates that the ALWAYS® Ultra Thin Long Maxi pad was made according to one of more of the following U.S. patents: U.S. Pat. Nos. 4,342,314; 4,463,045; 4,589,876; 4,687,478; 4,950,264; 5,009,653; 5,267,992; 5,354,400; 5,389,094; 5,413,568; 5,462,166; 5,489,283; 5,518,801; 5,620,430; 5,704,930; and Reissue 32,649.

One longitudinal side of the cover (topsheet) was cut and peeled back to permit access to the absorbent core. An acrylic plastic sheet about 5 mm thick was placed between the readily separable upper layer and the lower layer of the absorbent core to permit slitting of the upper layer only with a rotary knife. As in Example 1, longitudinally centered longitudinal slits, also transversely centered about the longitudinal centerline, were provided in the crotch region having a length of 7 cm and being inset 1.2 cm from the longitudinal sides of the top layer of the absorbent core at the transverse centerline. A section of white impervious barrier material, free of adhesive unlike the similar barrier material in Example 1, was cut to a length of 6.6 cm and a width of about 7.2 cm, marginally wider than the crotch region of the article. The two parallel slits defined a central portion of the unitary absorbent layer therebetween, the unitary absorbent layer being defined as the upper layer provided with slits, and also established an outer portion in the upper layer. The 1.2 cm-wide crotch region portions of the outer portion of the unitary absorbent layer were covered by the barrier material (i.e., it was disposed on the body-side surface of the outer portion in the crotch region), and the barrier material then descended into the slits and passed beneath the central portion of the unitary absorbent layer. A pledget of fluff pulp, essentially identical to that use in Example 1, was placed under the central portion of the unitary absorbent layer to provide increased shaping of the article.

Two-sided adhesive tape was used to attach the wicking barrier to the crotch region portions of the outer portion of the unitary absorbent layer, and further used to rejoin the topsheet to the longitudinal sides of the absorbent core in the region where the topsheet had been cut.

Example 3

Example 3 was made using a commercially available maxipad, the ALWAYS® Maxi with Wings with a DRI-WEAVE™ apertured film cover, manufactured by Procter and Gamble (Cincinnati, Ohio) and taken from a package of 20. This product also features "side channels" which are crescent-shaped, highly densified regions along the longitudinal sides in the crotch region contiguous with the high bulk, high thickness fluff pad that extends across the longitudinal length of the article. According to the package, the product was made under one of more of the following U.S. Pat. Nos. 4,342,314 and 4,463,045; 4,556,146; 4,573,986; 4,589,876; 4,687,478; and 5,267,992.

FIG. 15 depicts the original pad 150 as purchased, showing a unitary absorbent core 651 comprising a high-bulk fluff pad region 152, densified outer zones 154 of fluff contiguous with the high-bulk fluff pad region 152, the densified outer zones 154 apparently having a lower basis weight than the high-bulk fluff pad region 152, with highly densified embossment lines 155', 155" joining the high-bulk fluff pad region 152 to the densified outer zones 154. The topsheet (not shown) joins the backsheet 14 to form an outer rim, which is also attached to wings 158.

Steps were then taken to convert the commercial article into a pad with a wicking barrier separating a central portion 22 of the unitary absorbent layer 18 from an outer portion 20, with the fluff pad serving as a unitary absorbent layer 18. The result of these steps is shown as article 150 in FIG. 16, which follows the numbering scheme of FIG. 15. The apertured film topsheet (not shown) was torn near the outer perimeter of the wings 158 of the article 150, and by hand the airfelt core was torn to define a continuous slit 26 beginning with a transverse tear 174 at a longitudinal side of the unitary absorbent layer 18 near one end of the absorbent article 150, the transverse tear 174 extending transversely across a first embossment line 155' and across the unitary absorbent layer 18 until encountering the opposing embossment line 155". Tearing in the transverse direction ceased and was redirected along the embossment line 155" toward the opposing end of the absorbent article 150 until most but not all of the embossment line 155" had been torn. Tearing ceased and then commended again along the first embossment line 155' from the transverse portion of the tear 174 toward the opposing end of the article 150. In this manner, the slit 26 as shown had a transverse slit component 36 and two substantially longitudinal slit components 32, 34. The slit 26 was created without severing the densified outer zones 154 from the unitary absorbent layer 18, which therefore remained unitary. The continuous slit 26 largely circumscribed a central portion 22, separating it from an outer portion 20 of the unitary absorbent layer 18. Then the central portion 22 of the unitary absorbent layer 18 was lifted up, remaining attached to the outer portion 20 across a joining zone 28. An impervious wicking barrier 30 consisting of an 18-gsm 1-mil white poly film with a length of 6.5 cm and width of 10 cm was placed across the crotch region of the article 150 and the central portion 22 was lowered back into place, such that the wicking barrier 30 passed underneath the central portion 22 of the unitary absorbent layer 18 while covering a major portion of the body-side surface of the densified outer zones 154 in the crotch region. The wicking barrier 30 extended slightly past the outer perimeter of the densified outer zones 154, as depicted in FIG. 16. The wicking barrier 30 has a horizontal component 38 on the densified outer zones 154 and spans a vertical distance from the top of the densified outer zones 154 (which serve as the outer portion of the unitary absorbent layer 18) to the backsheet 14 beneath the central portion 22 of the unitary absorbent layer 18.

This modification of a commercial product can effectively reduce leaking from the central portion 22 to the outer portion 20 and particularly to the densified outer zones 154 within the outer portion 20 of the unitary absorbent layer 18, and can reduce bending stiffness and enhance the folding geometry of the article when worn. Similar modifications may be made with other commercial articles, such as pantiliners. The body fit performance of the modified article could be further enhanced by placing a central rising member (not shown) beneath the central portion 22.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent article for use on the body of a wearer, the absorbent article having, a longitudinal centerline, two longitudinal sides, a target zone and a body side, the absorbent article comprising:
   a) a liquid impervious backsheet;
   b) a liquid pervious topsheet attached to the backsheet;
   c) an absorbent core having a body-side surface disposed between the topsheet and the backsheet, the absorbent core comprising a unitary absorbent layer having a thickness and a width in the target zone of the absorbent article, the unitary absorbent layer comprising a central portion, an outer portion surrounding the central portion, and a boundary between the outer portion and the central portion, the boundary including one or more slits passing through the thickness of the unitary absorbent layer, the outer portion and the central portion each having a body-side surface and a garment-side surface; and
   d) a wicking barrier spanning a horizontal distance above the body-side surface of the outer portion of the unitary absorbent layer and spanning a vertical distance in the one or more slits of the unitary absorbent layer, wherein the wicking barrier is at least one selected from a group consisting of substantially liquid impervious and hydrophobic material impregnated.

2. The absorbent article of claim 1, wherein the wicking barrier spans the entire thickness of the unitary absorbent layer.

3. The absorbent article of claim 1, wherein the central portion of the unitary absorbent layer has a pair of longitudinal sides each having a length, with a majority of the length of each side circumscribed by more than one slit.

4. The absorbent article of claim 1, wherein the central portion of the unitary absorbent layer has a pair of longitudinal sides each having a length, with a majority of the length of each side circumscribed by one slit.

5. The absorbent article of claim 1, wherein the central portion has three or more sides and at least two of said sides are separated from the outer portion of the unitary absorbent layer by one slit.

6. The absorbent article of claim 1, wherein the central portion has at least one pair of opposing sides and one of the one or more slits substantially separates at least the one pair of opposing sides of the central portion of the unitary absorbent layer from the outer portion of the unitary absorbent layer.

7. The absorbent article of claim 1, wherein the unitary absorbent layer further comprises a longitudinal centerline and substantially resides in a plane, wherein a rectangle in the plane of the unitary absorbent layer, substantially aligned with the longitudinal centerline of the article and fitting within the boundary between the central portion and the outer portion of the unitary absorbent layer, can have exactly three sides that are blocked by the one or more slits, such that a line extending outward in the plane of the unitary absorbent layer normal to any blocked side will intercept one of the slits.

8. The absorbent article of claim 1, wherein one of the one or more slits comprises a first substantially longitudinal segment, a substantially transverse segment, and a second substantially longitudinal segment, the first and second substantially longitudinal segments being spaced apart about the longitudinal centerline of the absorbent article, the slit defining a majority of the boundary between the outer portion and the central portion of the unitary absorbent layer.

9. The absorbent article of claim 1, wherein the central portion has a substantially rectangular shape and one slit circumscribes two or more sides of the rectangular central portion.

10. The absorbent article of claim 1, wherein the central portion has a substantially triangular shape and one slit circumscribes two or more sides of the triangular central portion.

11. The absorbent article of claim 1, wherein the central portion has two opposing sides and the opposing sides are separated by one slit.

12. The absorbent article of claim 1, wherein the one or more slits form a shape selected from a "V" shape, a "U" shape, a "S" shape, a "H" shape, an upper portion of a bread loaf shape, three sides of a rectangle, an outer perimeter of a spiral, an upper portion of an hourglass, an upper portion of a half-rounded rectangle, and an ellipse truncated at one end.

13. The absorbent article of claim 1, wherein the one or more slits circumscribe all but a substantially linear hinge zone of the central portion of the unitary absorbent layer such that a majority of the central portion of the unitary absorbent layer can be lifted away from the outer portion of the unitary absorbent layer.

14. The absorbent article of claim 1, wherein the wicking barrier passes beneath the central portion of the unitary absorbent layer.

15. The absorbent article of claim 1, further comprising a hinge zone joining the central portion to the outer portion.

16. The absorbent article of claim 1, further comprising a plurality of hinge zones joining the central portion to the outer portion.

17. The absorbent article of claim 1, wherein the wicking barrier spans a horizontal distance in contact with the body-side surface of the absorbent core.

18. The absorbent article of claim 1, wherein the wicking barrier comprises a polymeric web.

19. The absorbent article of claim 1, wherein the wicking barrier comprises a single section of a polymeric film spanning a vertical distance in one or more the slits of at least about 2 mm and a horizontal distance above the body-side surface of the outer portion of the unitary layer of at least about 2 mm.

20. The absorbent article of claim 1 wherein the wicking barrier comprises a hydrophobic impregnate.

21. The absorbent article of claim 1, wherein the boundary has a joining zone between the central portion and the outer portion of the unitary absorbent layer, wherein the joining zone is treated with the hydrophobic impregnate.

22. The absorbent article of claim 1, wherein the wicking barrier comprises a hot melt impregnated into the unitary absorbent layer.

23. The absorbent article of claim 1, wherein the wicking barrier is unitary.

24. The absorbent article of claim 1, wherein the wicking barrier is non-unitary.

25. The absorbent article of claim 1, wherein the central portion has a width equal to about 80% or less of the width of the unitary absorbent layer in the target zone.

26. The absorbent article of claim 1, further comprising a second absorbent layer disposed above the unitary absorbent layer.

27. The absorbent article of claim 26, wherein the second absorbent layer has a body-side surface and the wicking barrier spans a horizontal distance on the body-side surface of the second absorbent layer.

28. The absorbent article of claim 1, further comprising a second absorbent layer disposed below the unitary absorbent layer.

29. The absorbent article of claim 1, further comprising a deflection control element.

30. The absorbent article of claim 29, wherein the deflection control element is disposed within the central portion of the unitary absorbent layer.

31. The absorbent article of claim 29, wherein the deflection control element is disposed beneath the central portion of the unitary absorbent layer.

32. The absorbent article of claim 29, wherein the deflection control element comprises a central rising member.

33. The absorbent article of claim 29, wherein the deflection control element comprises a central inflatable member.

34. The absorbent article of claim 29, wherein the deflection control element comprises a narrow absorbent pledget disposed below the central portion of the unitary absorbent layer, the pledget having a sufficient thickness to predispose the central portion of the unitary absorbent layer to deflect upward during lateral compression.

35. The absorbent article of claim 29, wherein the deflection control element comprises bending lines in the absorbent core.

36. The absorbent article of claim 1, wherein the unitary absorbent layer further comprises a garment-side surface and a pair of spaced apart slits, and wherein the wicking barrier descends through one of the pair of slits, extends below the garment-side surface of the central portion of the unitary absorbent layer, and further ascends through the other one of the pair of slits.

37. The absorbent article of claim 36, wherein the wicking barrier extends a horizontal distance on the body-side surface of the outer portion of the unitary absorbent layer, extending laterally outward from each of the pair of spaced apart slits.

38. The absorbent article of claim 1 wherein the wicking barrier is at least substantially liquid impervious.

39. An absorbent article for use on the body of a wearer, the absorbent article having two longitudinal sides, a target zone and a body side, the absorbent article comprising:
 a) a liquid impervious backsheet;
 b) a liquid pervious topsheet attached to the backsheet;
 c) a unitary absorbent layer disposed between the topsheet and the backsheet, the unitary absorbent layer having a thickness, and comprising a central portion and an outer portion surrounding the central portion, the central portion and the outer portion separated by a boundary comprising a slit, the outer portion having a body-side surface; and
 d) a wicking barrier spanning a horizontal distance on the surface of the outer portion of the unitary absorbent layer and spanning the thickness of the unitary absorbent layer in a portion of the slit, wherein the wicking barrier is at least one selected from a group consisting of substantially liquid impervious and hydrophobic material impregnated.

40. The absorbent article of claim 39, further comprising a deflection control element in cooperative association with the central portion of the unitary absorbent layer, wherein lateral compression causes the central portion to deflect away from the backsheet.

41. The absorbent article of claim 39 wherein the wicking barrier is at least substantially liquid impervious.

42. An absorbent article for use on the body of a wearer, the absorbent article having, a longitudinal centerline, two longitudinal sides, a target zone and a body side, the absorbent article comprising:
 a) a liquid impervious backsheet;
 b) a liquid pervious topsheet attached to the backsheet;
 c) an absorbent core having a body-side surface disposed between the topsheet and the backsheet, the absorbent core comprising a unitary absorbent layer having a thickness and a width in the target zone of the absorbent article, the unitary absorbent layer comprising a central portion, an outer portion, and a boundary between the outer portion and the central portion, the boundary including one or more slits passing through the thickness of the unitary absorbent layer, the outer portion and the central portion each having a body-side surface and a garment-side surface; and
 d) a wicking barrier spanning a horizontal distance above the body-side surface of the outer portion of the unitary absorbent layer and spanning a vertical distance in the one or more slits of the unitary absorbent layer, wherein the wicking barrier is liquid impervious.

43. The absorbent article of claim 42, wherein the wicking barrier spans the entire thickness of the unitary absorbent layer.

44. The absorbent article of claim 42, wherein the central portion of the unitary absorbent layer has a pair of longitudinal sides each having a length, with a majority of the length of each side circumscribed by more than one slit.

45. The absorbent article of claim 42, wherein the central portion of the unitary absorbent layer has a pair of longitudinal sides each having a length, with a majority of the length of each side circumscribed by one slit.

46. The absorbent article of claim 42, wherein the central portion has three or more sides and at least two of said sides are separated from the outer portion of the unitary absorbent layer by one slit.

47. The absorbent article of claim 42, wherein the central portion has at least one pair of opposing sides and one of the one or more slits substantially separates at least the one pair of opposing sides of the central portion of the unitary absorbent layer from the outer portion of the unitary absorbent layer.

48. The absorbent article of claim 42, wherein the unitary absorbent layer further comprises a longitudinal centerline and substantially resides in a plane, wherein a rectangle in the plane of the unitary absorbent layer, substantially aligned with the longitudinal centerline of the article and fitting within the boundary between the central portion and the outer portion of the unitary absorbent layer, can have exactly three sides that are blocked by the one or more slits, such that a line extending outward in the plane of the unitary absorbent layer normal to any blocked side will intercept one of the slits.

49. The absorbent article of claim 42, wherein one of the one or more slits comprises a first substantially longitudinal segment, a substantially transverse segment, and a second substantially longitudinal segment, the first and second substantially longitudinal segments being spaced apart about the longitudinal centerline of the absorbent article, the slit defining a majority of the boundary between the outer portion and the central portion of the unitary absorbent layer.

50. The absorbent article of claim 42, wherein the central portion has a substantially rectangular shape and one slit circumscribes two or more sides of the rectangular central portion.

51. The absorbent article of claim 42, wherein the slit circumscribes two or more sides of a substantially triangular central portion of the unitary absorbent layer.

52. The absorbent article of claim 42, wherein the central portion has two opposing sides and the opposing sides are separated by one slit.

53. The absorbent article of claim 42, wherein the one or more slits form a shape selected from a "V" shape, a "U" shape, a "S" shape, a "H" shape, an upper portion of a bread loaf shape, three sides of a rectangle, an outer perimeter of a spiral, an upper portion of an hourglass, an upper portion of a half-rounded rectangle, and an ellipse truncated at one end.

54. The absorbent article of claim 42, wherein the one or more slits circumscribe all but a substantially linear hinge zone of the central portion of the unitary absorbent layer such that a majority of the central portion of the unitary absorbent layer can be lifted away from the outer portion of the unitary absorbent layer.

55. The absorbent article of claim 42, wherein the wicking barrier passes beneath the central portion of the unitary absorbent layer.

56. The absorbent article of claim 42, further comprising a hinge zone joining the central portion to the outer portion.

57. The absorbent article of claim 42, further comprising a plurality of hinge zones joining the central portion to the outer portion.

58. The absorbent article of claim 42, wherein the wicking barrier spans a horizontal distance in contact with the body-side surface of the absorbent core.

59. The absorbent article of claim 42, wherein the wicking barrier comprises a polymeric web.

60. The absorbent article of claim 42, wherein the wicking barrier comprises a single section of a polymeric film spanning a vertical distance in one or more the slits of at least about 2 mm and a horizontal distance above the body-side surface of the outer portion of the unitary layer of at least about 2 mm.

61. The absorbent article of claim 42 wherein the wicking barrier comprises a hydrophobic impregnate.

62. The absorbent article of claim 42, further comprising a joining zone between the central portion and the outer portion of the unitary absorbent layer, wherein the joining zone is treated with the hydrophobic impregnate.

63. The absorbent article of claim 42, wherein the wicking barrier comprises a hot melt impregnated into the unitary absorbent layer.

64. The absorbent article of claim 42, wherein the wicking barrier is unitary.

65. The absorbent article of claim 42, wherein the wicking barrier is non-unitary.

66. The absorbent article of claim 42, wherein the central portion has a width equal to about 80% or less of the width of the unitary absorbent layer in the target zone.

67. The absorbent article of claim 42, further comprising a second absorbent layer disposed above the unitary absorbent layer.

68. The absorbent article of claim 42, further comprising a second absorbent layer disposed above the unitary absorbent layer, the second absorbent layer further comprising a body-side surface and the wicking barrier spanning a horizontal distance on the body-side surface of the second absorbent layer.

69. The absorbent article of claim 42, further comprising a second absorbent layer disposed below the unitary absorbent layer.

70. The absorbent article of claim 42, further comprising a deflection control element.

71. The absorbent article of claim 42, wherein the deflection control element is disposed within the central portion of the unitary absorbent layer.

72. The absorbent article of claim 42, wherein the deflection control element is disposed beneath the central portion of the unitary absorbent layer.

73. The absorbent article of claim 42, wherein the deflection control element comprises a central rising member.

74. The absorbent article of claim 42, wherein the deflection control element comprises a central inflatable member.

75. The absorbent article of claim 42, wherein the deflection control element comprises a narrow absorbent pledget disposed below the central portion of the unitary absorbent layer have sufficient thickness to predispose the central portion of the unitary absorbent layer to deflect upward during lateral compression.

76. The absorbent article of claim 42, wherein the deflection control element comprises bending lines in the absorbent core.

77. The absorbent article of claim 42, wherein the unitary absorbent layer further comprises a garment-side surface and a pair of spaced apart slits, and wherein the wicking barrier descends through one of the pair of slits, extends below the garment-side surface of the central portion of the unitary absorbent layer, and further ascends through the other one of the pair of slits.

78. The absorbent article of claim 77, wherein the wicking barrier extends a horizontal distance on the body-side surface of the outer portion of the unitary absorbent layer, extending laterally outward from each of the pair of spaced apart slits.

79. An absorbent article for use on the body of a wearer, the absorbent article having two longitudinal sides, a target zone and a body side, the absorbent article comprising:

a) a liquid impervious backsheet;

b) a liquid pervious topsheet attached to the backsheet;

c) a unitary absorbent layer disposed between the topsheet and the backsheet, the unitary absorbent layer having a thickness, and comprising a central portion and an outer portion separated by a boundary comprising a slit, the outer portion having a body-side surface; and d) a wicking barrier spanning a horizontal distance on the surface of the outer portion of the unitary absorbent layer and spanning the thickness of the unitary absorbent layer in a portion of the slit, wherein the wicking barrier is liquid impervious.

* * * * *